(12) United States Patent
Keiser

(10) Patent No.: US 8,523,789 B2
(45) Date of Patent: Sep. 3, 2013

(54) SYSTEM FOR TESTING MUSCULAR POWER

(75) Inventor: Dennis L. Keiser, Sanger, CA (US)

(73) Assignee: Keiser Corporation, Fresno, CA (US)

( * ) Notice: Subject to any disclaimer, the term of this patent is extended or adjusted under 35 U.S.C. 154(b) by 1522 days.

(21) Appl. No.: 10/694,198

(22) Filed: Oct. 27, 2003

(65) Prior Publication Data

US 2004/0250618 A1    Dec. 16, 2004

Related U.S. Application Data

(60) Provisional application No. 60/478,499, filed on Jun. 14, 2003, provisional application No. 60/479,093, filed on Jun. 16, 2003, provisional application No. 60/482,911, filed on Jun. 25, 2003.

(51) Int. Cl.
*A61B 5/103* (2006.01)
*A61B 5/117* (2006.01)
*A63B 15/02* (2006.01)

(52) U.S. Cl.
USPC ............................................. 600/595; 482/1

(58) Field of Classification Search
USPC ............... 600/587, 595; 73/379.01, 379.09, 73/379.08; 482/1–9
See application file for complete search history.

(56) References Cited

U.S. PATENT DOCUMENTS

| | | | | |
|---|---|---|---|---|
| 3,848,467 A | * | 11/1974 | Flavell | 482/4 |
| 4,050,310 A | | 9/1977 | Keiser | 73/379 |
| 4,257,593 A | | 3/1981 | Keiser | 272/130 |
| 4,601,468 A | * | 7/1986 | Bond et al. | 482/7 |
| 4,730,829 A | * | 3/1988 | Carlson | 482/5 |
| 4,805,455 A | | 2/1989 | DelGiorno et al. | |
| 4,842,274 A | | 6/1989 | Oosthuizen et al. | |
| 4,846,466 A | * | 7/1989 | Stima, III | 482/112 |
| 4,905,676 A | | 3/1990 | Bond et al. | |

(Continued)

FOREIGN PATENT DOCUMENTS

| | | |
|---|---|---|
| DE | 40 31 481 A1 | 10/1990 |
| EP | 0 199 442 | 10/1986 |

(Continued)

OTHER PUBLICATIONS

*KEISER® Technical Information on A400 Software Version V3.15*, Oct. 2, 1997, 4 pages.

(Continued)

*Primary Examiner* — Max Hindenburg
*Assistant Examiner* — Jonathan M Foreman
(74) *Attorney, Agent, or Firm* — Knobbe Martens Olson & Bear, LLP

(57) ABSTRACT

An apparatus and method evaluate the power of a muscle or a muscle group by initializing a resistance element to a first resistance level. An engagement assembly coupled to the resistance element is moved at a highest achievable velocity through an exercise stroke while a representative velocity at which the engagement assembly is moved through the exercise stroke is measured. At the completion of the exercise stroke, the resistance level of the resistance element is increased and the exercise stroke is repeated. The resistance level is increased until the resistance level is sufficient to preclude moving the engagement assembly through a complete exercise stroke. The power for each exercise stroke, the maximum power and the velocity and resistance at which the maximum power is produced are calculated based on the resistance level for each exercise stroke and the representative velocity for each exercise stroke.

11 Claims, 11 Drawing Sheets

(56) References Cited

U.S. PATENT DOCUMENTS

| | | | |
|---|---|---|---|
| 4,907,797 A | 3/1990 | Gezari et al. | 272/129 |
| 5,209,223 A | 5/1993 | McGorry et al. | 128/25 R |
| 5,336,145 A | 8/1994 | Keiser | 482/54 |
| 5,526,692 A | 6/1996 | Keiser | 73/715 |
| 5,722,937 A | 3/1998 | Smith | 601/23 |
| 5,997,440 A * | 12/1999 | Hanoun | 482/10 |
| 6,027,429 A * | 2/2000 | Daniels | 482/5 |
| 6,231,481 B1 * | 5/2001 | Brock | 482/8 |
| 6,270,445 B1 * | 8/2001 | Dean et al. | 482/4 |
| 6,672,157 B2 * | 1/2004 | MacFarlane et al. | 73/379.01 |
| 2002/0025890 A1 | 2/2002 | Keiser | 482/92 |
| 2002/0086774 A1 * | 7/2002 | Warner | 482/8 |
| 2003/0115955 A1 | 6/2003 | Keiser | 73/379.06 |

FOREIGN PATENT DOCUMENTS

| | | |
|---|---|---|
| EP | 0 275 959 | 1/1988 |
| EP | 1 208 876 | 5/2002 |
| JP | 10085363 | 4/1998 |
| WO | WO 86/06947 | 12/1986 |
| WO | WO 03/041809 A2 | 5/2003 |

OTHER PUBLICATIONS

*KEISER® Documentation on the use of the CAPTURE program*, Apr. 1999, 6 pages.
*KEISER® A400 Software Manual*, Version 4.01, Apr. 1999, pp. 1-11.
*Keiser A420 Operations and Maintenance Manual*, Rev A, Jun. 28, 2002, pp. 1-23.
*iButton Overview*, Maxim/Dallas Semiconductor Corporation, 2002, 3 pages.
*iButton Applications*, Maxim/Dallas Semiconductor Corporation, 2002, 2 pages.
*When is a pound not a pound? Keiser compares iron and air*, Keiser Corporation, Fresno, California, 2001, pp. 1-4.
*Strength Training and Aging*, Research Abstracts, Keiser Institute on Aging, 1999, pp. 1-67 and inside cover article.
International Search Report, mailed Feb. 2, 2005.
International Search Report for application No. PCT/US2005/013290 mailed on Apr. 19, 2005.

\* cited by examiner

FIG. 7   ROUTINE REPEATED 400 TIMES PER SECOND

SYSTEM FOR TESTING MUSCULAR POWER

RELATED APPLICATIONS

The present application claims the benefit of priority under 35 U.S.C. §119(e) of U.S. Provisional Application No. 60/478,499, filed on Jun. 14, 2003, U.S. Provisional Application No. 60/479,093, filed on Jun. 16, 2003, and U.S. Provisional Application No. 60/482,911, filed on Jun. 25, 2003.

BACKGROUND OF THE INVENTION

1. Field of the Invention

The present invention is applicable to the fields of fitness, exercise, physical rehabilitation, sports medicine and extremity testing and is directed to methods and apparatuses useable in such fields.

2. Description of the Related Art

Numerous devices have been developed to increase the strength, agility and quickness of athletes and other persons. In addition to enhancing the performance of athletes, such devices are used to improve or maintain the fitness and health of non-athletes, both to enhance the lifestyles of non-athletes and to potentially increase their respective life spans. Such devices range from basic equipment such as barbells, dumbbells, and the like, to increasingly more complex equipment such as universal gyms which enable a user to quickly modify the weights or resistances being used to exercise the user's muscles. See, for example, U.S. Pat. Nos. 4,257,593, 5,526, 692 and 5,336,145 to Dennis L. Keiser and U.S. patent application Publication No. US 2002/0024590 A1, which describe exercising apparatuses and related devices using pneumatic devices to provide controllable resistances, and which are incorporated by reference herein. In particular, such pneumatic exercising apparatuses advantageously reduce or eliminate the inertial effects of conventional weights wherein the force required to start moving a weight and the tendency of the weights to continue moving cause the forces required during each exercising stroke to vary throughout the stroke. Such pneumatic apparatuses provide a generally constant resistance throughout the exercising stroke.

In addition to being used for the development of strength, agility and quickness, exercising apparatuses can be used to measure strength, agility and quickness of a person. For example, a person's ability to lift weights against the force of gravity or a corresponding ability to move against a resistance can be measured at different times to determine whether such characteristics are improving in response to an exercise program or in response to therapy. Such measurements can also be used for evaluation purposes to determine whether one or more muscles or muscle groups are not performing adequately so that a therapist or a fitness trainer, for example, can develop a program of therapy or training more specifically directed to the inadequately performing muscles.

Historically, measurement and evaluation of muscular performance have concentrated on measuring the strength of a muscle or muscle group (e.g., measuring the amount of weight that can be lifted). However, it has been determined that strength alone does not accurately represent the performance of muscles. A person's muscles may be able to lift an adequate amount of weight, but may be too slow to be useful for many purposes. For example, an athlete putting the shot at a track and field contest must have the strength to easily move the sixteen-pound shot; however, the strength must be coupled with sufficient speed to cause the shot to be propelled with enough velocity to travel in excess of 70 feet (e.g., 70 feet, 11.25 inches by Randy Barnes at the 1996 Atlanta Olympics). In contrast, some activities require the ability to move very heavy objects at much lower velocities. Thus, although the power requirements may be similar for two activities, the forces and velocities at which the maximum power is required may be different for the two activities.

From the foregoing it should be understood that a more meaningful measurement of the performance of a person's muscles is a measurement of power (e.g., a measurement of the force applied by the muscles times the velocity of the movement). The average power over an exercise stroke, for example, can be accomplished by timing the duration of the stroke and measuring the distance traveled to determine the average velocity, and then multiplying the average velocity by the force (e.g., the weight moved or the resistance overcome by the muscles). However, because of the structure of most appendages in a person's body, the speed of an exercise stroke will vary throughout the stroke as the appendage varies from full extension to full contraction and the leverage of the muscles against the moving portion of the appendage changes.

SUMMARY OF THE INVENTION

In view of the foregoing, it can be seen that a need exists for measuring the power exerted by a person's muscles in order to determine the condition of the person's muscles. In addition to determining the maximum power delivered by the muscles, a need exists for determining the force and velocity at which the maximum power is delivered. In some cases, a need also exists for determining the position of the muscles when the maximum power is delivered (e.g., where the muscle and the associated appendage are between maximum extension and maximum contraction).

In accordance with an aspect of the present invention, a method of evaluating the power of a muscle or a muscle group comprises the act of initializing a resistance element to a first resistance level. The resistance element is coupled to an engagement assembly. The muscle or muscle group to be evaluated is caused to move the engagement assembly at a highest achievable velocity through an exercise stroke. While the exercise stroke is occurring, a representative velocity at which the engagement assembly is moved through the exercise stroke is measured. At the completion of the exercise stroke, the resistance level of the resistance element is increased. The acts of moving, measuring and increasing are repeated until the resistance level is sufficient to preclude moving the engagement assembly through a complete exercise stroke. After the last successful exercise stroke, a power for each exercise stroke is calculated based on the resistance level for each exercise stroke and based on a representative velocity for each exercise stroke. A maximum power is determined, and a velocity and a resistance level where the maximum power is produced are also determined. Preferably, the resistance element is a pneumatic cylinder in which the engagement assembly causes a piston within the pneumatic cylinder to move against air pressure in the pneumatic cylinder. In one particular embodiment, the engagement assembly is configured as a chest press, wherein a first handgrip is provided for a left hand of a subject and a second handgrip is provided for a right hand of a subject. Each handgrip is coupled to a respective resistance element, and the velocities are measured independently for each handgrip to provide an independent power measurement for each arm of the subject. Preferably, the time between the act of measuring selectively increases as the resistance level increases to enable the muscle group to rest between successive acts of moving the engagement assembly. Preferably, the velocity is determined by periodically measuring a position of a piston in a pneumatic cylinder, and the velocity is calculated based on the distance moved during a known time interval.

In accordance with another aspect of the present invention, a system for evaluating the power of a muscle group comprises a variable resistance element that can be adjusted to a plurality of resistance levels. An engagement assembly is coupled to the resistance element. During an exercise stroke, the engagement assembly moves against the resistance applied against the engagement by the resistance element. A position transducer is sampled at predetermined time intervals to enable determination of a representative velocity at which the engagement assembly is moved through the exercise stroke at a highest achievable velocity for the applied resistance level. A power calculation system calculates the power for each exercise stroke based on the applied resistance level for each exercise stroke and based on the representative velocity for each exercise stroke. The power calculation system determines a maximum power and determines a velocity and a resistance level at which the maximum power is produced. Preferably, the resistance element is a pneumatic cylinder in which the engagement assembly causes a piston within the pneumatic cylinder to move against air pressure in the pneumatic cylinder. In a particular embodiment, the engagement assembly is configured as a chest press having a first handgrip for a left hand of a subject and having a second handgrip for a right hand of the subject. In the preferred embodiment, the variable resistance element comprises a first resistance element coupled to the first handgrip and a second resistance element coupled to the second handgrip. Each resistance element includes a respective position transducer. In the preferred embodiment, the power calculation system calculates the power independently for each arm of the subject.

BRIEF DESCRIPTION OF THE DRAWINGS

Preferred embodiments of the present invention are described below in connection with the accompanying drawing figures in which.

DETAILED DESCRIPTION OF THE PREFERRED EMBODIMENTS

Figure 1:
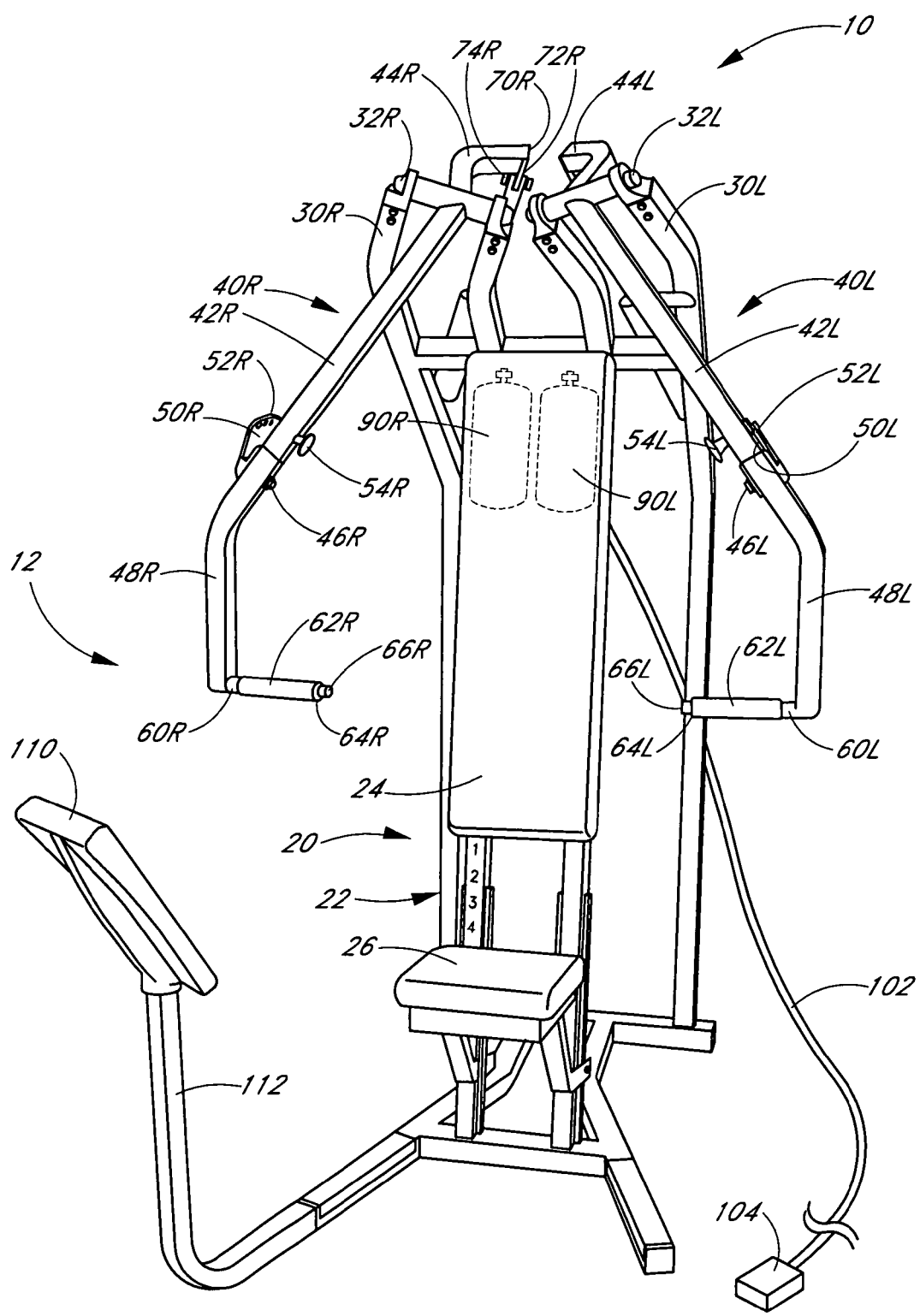
FIG. 1 illustrates a front view of an exercise and evaluation apparatus in accordance with a preferred embodiment.

FIGS. 1, 2, 3 and 4 illustrate an embodiment of an exemplary exercise apparatus 10 that can be used advantageously in connection with embodiments of the present invention for evaluating power generated by a muscle group when moving against levels of resistance that are varied to correspond to varying weights. Although described herein with respect to the apparatus 10, it should be understood that embodiments of the present invention can be incorporated into other exercise apparatuses. For example, the apparatus 10 is configured as a "chest press." The apparatus 10 can also be configured in other suitable configurations. Examples of other exercise equipment on which the performance measurement system can be used include, without limitation, a leg press, a leg extension machine, a leg curl machine, a standing hip machine, an abdominal machine, a lower back machine, an upper back machine, a lateral pull down machine, a military press machine, a triceps machine, an arm curl machine, a seated butterfly machine, a seated calf machine, a lateral shoulder raise machine, a squat machine, and a hip abductor machine, such as the types available commercially from Keiser Corporation, Fresno, Calif.

The apparatus 10 comprises a frame 12 having a lower portion that rests on a floor of an exercise facility or a fitness evaluation facility. The frame 12 has a generally vertical front portion 20 that supports a seat assembly 22. The seat assembly 22 comprises a seat back portion 24 and a seat bottom portion 26. Preferably, the seat bottom portion 24 is adjustable vertically to accommodate variations in the physical characteristics of users. In alternative embodiments, the seat back portion 26 is also adjustable to accommodate variations in lengths of the users' arms.

Figure 2:
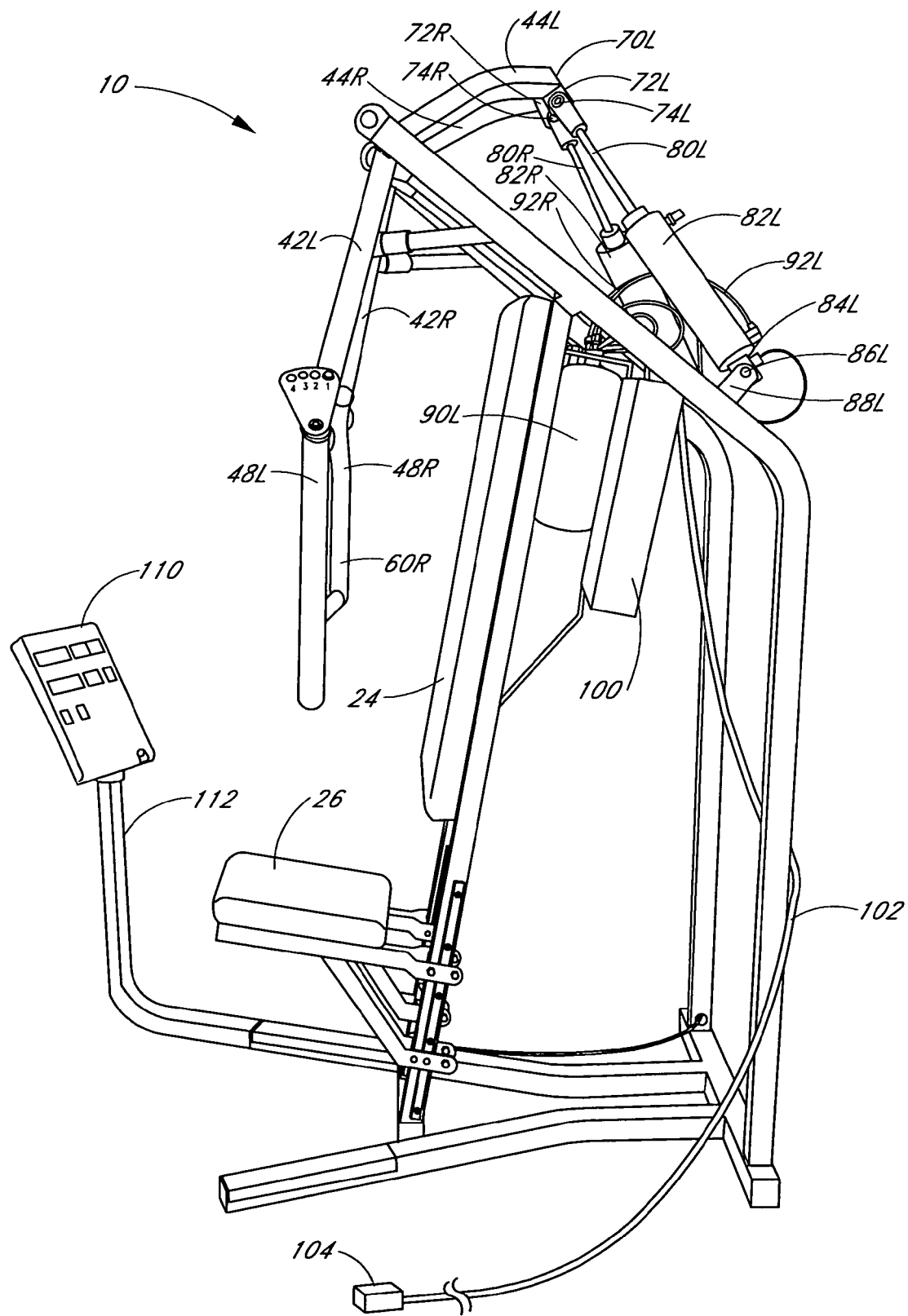
FIG. 2 illustrates a side view of the exercise and evaluation apparatus of FIG. 1.
Figure 3:
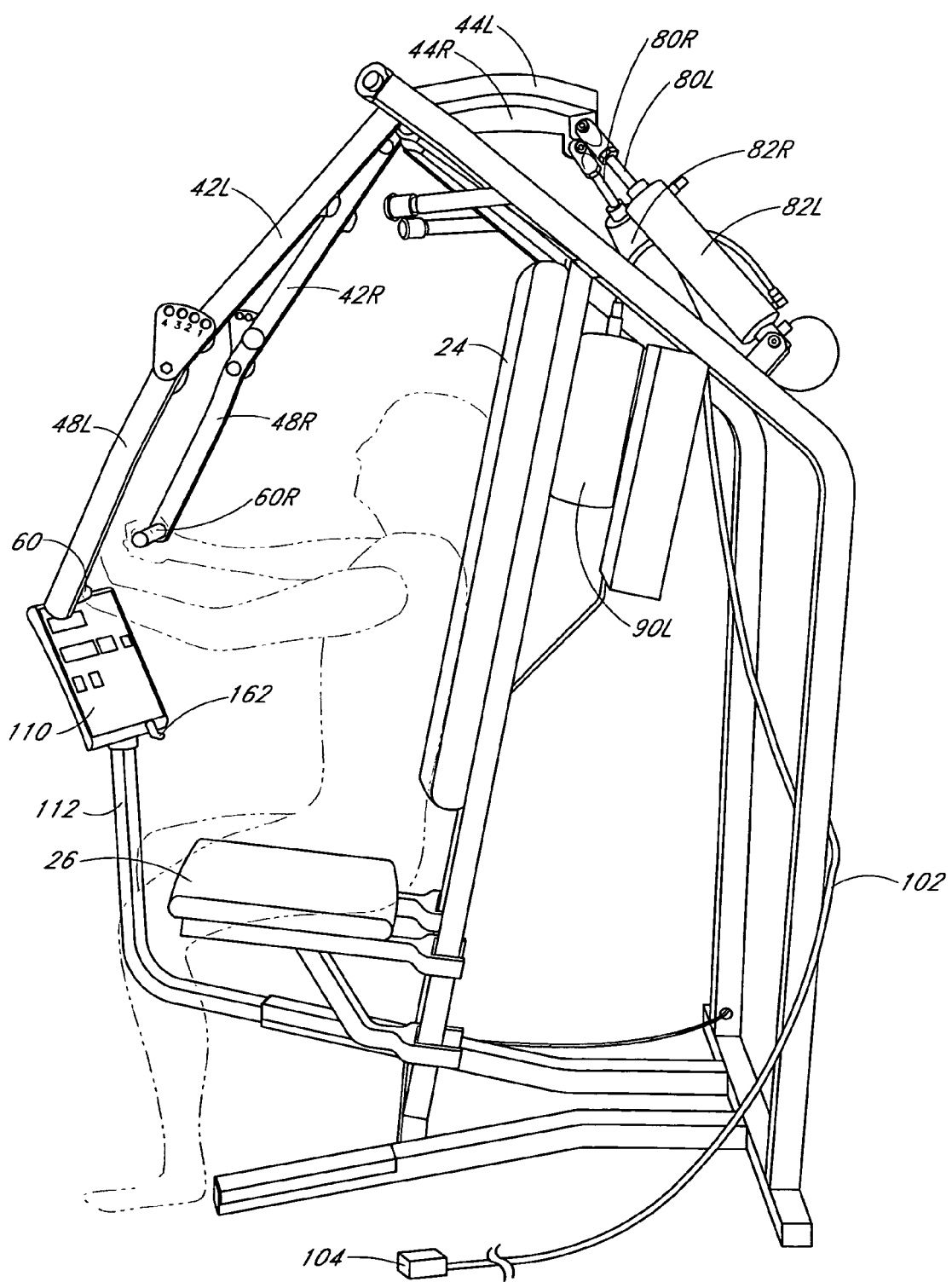
FIG. 3 illustrates a side view of the exercise and evaluation apparatus of FIGS. 1 and 2 with the position of a user of the apparatus shown in phantom.

The frame 12 includes a left top portion 30L and a right top portion 30R. The two top portions 30L, 30R are cantilevered over the seat assembly 22. The left top portion 30L has a left hinge 32L positioned at the most forward and upward end. Similarly, the right top portion 30R has a right hinge 32R positioned at the most forward and upward end. As used herein, "left" and "right" are defined with respect to the position of a user of the apparatus 10. Thus, when facing the front portion 20 as shown in FIG. 2, the left top portion 30L and the left hinge 32L are on the right side of the drawing figure, and the right top portion 30R and the right hinge 32R are on the left side of the drawing figure.

A left lever 40L is pivotally mounted to the left hinge 32L, and a right lever 40R is pivotally mounted to the right hinge 32R. As described below, the left lever 40L and the right lever 40R in combination with their respective components each comprises an independent engagement apparatus for coupling the power from a user to respective resistance elements. The resistance elements are preferably implemented by left and right pneumatic cylinders, which are also described below.

The left lever 40L comprises a lower lever portion 42L that extends generally below and slightly forward of the left hinge 32L. The left lever 40L further comprises an upper lever portion 44L that extends generally above and to the rear of the left hinge 32L. In the illustrated embodiment, the lower lever portion 42L and the upper lever portion 44L comprise a unitary structure having the left hinge 32L formed at an intermediary location of the structure such that when the lower lever portion 42L moves forward and generally upward, the upper lever portion 44L moves rearward and generally downward.

Preferably, the lower lever portion 42L includes a hinge 46L at the lower end thereof. An extended lever portion 48L pivotally mounted to the lower lever portion 42L via the hinge 46L. An adjustment selector 50L is mounted to the extended lever portion 48L at the location of the hinge 46L. The adjustment selector 50L has a plurality of holes 52L formed therein (e.g., four holes in the illustrated embodiment). The holes 52L are selectably engageable with a spring-loaded pin 54L near the lower end of the lower lever portion 42L. The spring-loaded pin 54L can be temporarily disengaged from one of the holes 52L and the extended lever portion 48L can be pivoted about the hinge 46L to change the angle of the extended lever portion 48L with respect to the lower lever portion 42L to adapt the position of the extended lever portion 48L to the physical characteristics of a particular user. The spring-loaded pin 54L is re-engaged the most closely aligned one of the holes 52L to restrain the extended lever portion 48L at the selected angle.

In like manner, the right lever 40R comprises elements that generally correspond to the elements of the left lever 40L. The elements of the right lever 40R are positioned in similar locations and operate in similar manners as the corresponding elements of the left lever 40L. In particular, the right lever 40R comprises a lower lever portion 42R, an upper lever portion 44R, a hinge 46R, and an extended lever portion 48R. An adjustment selector 50R has a plurality of holes 52R. A selectable one of the holes 52R is engageable with a spring-loaded pin 54R to adjust the angle of the extended lever portion 48R with respect to the lower lever portion 42R.

In alternative embodiments, the extended lever portions 48L, 48R may be positioned at a fixed angle with respect to the respective lower lever portions 42L, 42L such that the hinges 46L, 46R and the selectors 50L, 50R are not needed.

The left lever 40L includes a left handgrip 60L that extends inward (e.g., towards the right) from the left extended lever portion 48L. Similarly, the right lever 40R includes a right handgrip 60R that extends inward (e.g., towards the left) from the right extended lever portion 166. In the illustrated embodiment, the handgrips 60L, 60R are positioned generally perpendicularly to the respective extended lever portions 48L, 48R. Each handgrip 60L, 60R has a length sufficient to accommodate the width of a user's hand and to further accommodate variations in the position of a user's hand. Preferably, each handgrip 60L, 60R is cylindrical and has a respective gripping surface 62L, 62R mounted thereon to assist a user in grasping the handgrips. The gripping surfaces 62L, 62R may advantageously be padded for the comfort of the user's hands.

The exposed end 64L of the left handgrip 60L supports a left actuator button 66L. Similarly, the exposed end 64R of the right handgrip 60R supports a right actuator button 66R. By pressing one of the actuator buttons 66L or 66R or by pressing both buttons 66L and 66R, a user is able to control various aspects of the operation of the apparatus 10, which will be discussed below.

A user seated in the seat assembly 22 is able to grip the handgrips 60L, 60R and apply forward forces to the extended lower portions 48L, 48R of the levers 40L, 40R to cause the extended lower portions 48L, 48R to move generally forwardly and upwardly. The levers 40L, 40R pivot about the respective hinges 32L, 32R such the respective upper lever portions 44L, 44R move generally rearward and downward.

Note that in the illustrated embodiment, the left lever 40L and the right lever 40R operate substantially independently. For example, one lever can be moved while the other lever remains at rest. As a further example, the two levers can be moved at different rates.

A rearmost end 70L of the left upper lever portion 44L includes a left upper pivot mount 72L. The left upper pivot mount 72L supports a pivot pin 74L. A left connecting rod 80L extends from a first end of a left pneumatic cylinder 82L and is connected to the left upper lever portion 44L at the left upper pivot mount 72L via the pivot pin 74L.

A second end of the left pneumatic cylinder 82L includes a lug 84L having a pivot pin 86L mounted therein. The pivot pin 86L engages a left lower pivot mount 88L on a generally rearward portion of the left top portion 30L of the frame 12. Movement of the left upper lever portion 44L rearwardly and downwardly in response to forward force applied to the left handgrip 60L by a user causes the left connecting rod 80L to be moved into the left pneumatic cylinder 82L. An end (not shown) of the left connecting rod 80L comprises a piston that slides within the left pneumatic cylinder 82L. The left connecting rod 80L and the left pneumatic cylinder 82L comprise a linear actuator which functions as a resistance assembly for the left lever 40L. As the left connecting rod 80L moves into the left pneumatic cylinder 82L, the left connecting rod 80L pivots with respect to the left upper pivot mount 72L, and the second end of the left pneumatic cylinder 82L pivots with respect to the left lower pivot mount 88L so that the left connecting rod 80L can move freely with respect to the left pneumatic cylinder 82L without binding.

Similarly, an end 70R of the right upper lever portion 44R includes a right upper pivot mount 72R. The right upper pivot mount 72R supports a pivot pin 74R. A right connecting rod 80R extends from a first end of a right pneumatic cylinder 82R and is connected to the right upper lever portion 44R at the right upper pivot mount 72R via the pivot pin 72R.

A second end (not shown) of the right pneumatic cylinder 82R includes a lug (not shown) having a pivot pin (not shown) mounted therein. The pivot pin engages a right lower pivot mount (not shown) on a generally rearward portion of the right top portion 30R of the frame 12. Movement of the right upper lever portion 44R rearwardly and downwardly in response to forward force applied to the right handgrip 60R by a user causes the right connecting rod 80R to be moved into the right pneumatic cylinder 82R. An end (not shown) of the right connecting rod 80R comprises a piston that slides within the right pneumatic cylinder 82R. The right connecting rod 80R and the right pneumatic cylinder 82R comprise a linear actuator which functions as a resistance assembly for the right lever 40R. As the right connecting rod 80R moves into the right pneumatic cylinder 82R, the right connecting rod 80R pivots with respect to the right upper pivot mount 72R, and the second end of the right pneumatic cylinder 82R pivots with respect to the right lower pivot mount so that the right connecting rod 80R can move freely with respect to the right pneumatic cylinder 82R without binding.

Within each pneumatic cylinder 82L, 82R, the respective piston divides the cylinder body into two variable volume chambers. At least one of the chambers is a charged chamber that selectively communicates with a compressed air source (shown schematically in FIG. 5) and with the atmosphere so as to provide the desired resistance. The other chamber can be open to the atmosphere; however, in some applications, both chambers can be pressurized (e.g., be of equal pressure), can selectively communicate with the atmosphere and/or can communicate with each other. In the illustrated embodiment, however, one of the chambers communicates with the atmosphere so as not to resist movement of the piston.

The pneumatic cylinders 82L, 82R may be advantageously constructed from metal or other suitable materials. In one preferred embodiment, the pneumatic cylinders 82L, 82R and the internal pistons comprise a polymer (e.g., plastic) to reduce the manufacturing costs and the weight of the resistance assemblies.

In the illustrated embodiment, the respective connecting rod 80L, 80R extends through the variable volume chamber open to the atmosphere. The respective connecting rod 80L, 80R moves linearly along a stroke axis as the piston slides within the cylinder bore in the respective pneumatic cylinder 82L, 82R. The stroke lengths of the connecting rods 80L, 80R are sufficient to provide the desired strokes for the upper lever portions 44L, 44R.

In the illustrated embodiment, the internal chamber proximate the respective second end of each pneumatic cylinder 82L, 82R (e.g., the lower chamber of each cylinder) is pressurized. The lower chamber of the left pneumatic cylinder 82L communicates with at least one left accumulator 90L via a pneumatic tube 92L, as shown more clearly in FIG. 5. Similarly, the lower chamber of the right pneumatic cylinder 82R communicates with at least one right accumulator 90R via a pneumatic tube 92R. The two accumulators 90L, 90R are located behind the seat back portion 24 in the illustrated embodiment and are secured to the frame 12. The pneumatic tubes 92L, 92R function as respective air equalization lines that interconnect the accumulators 90L, 90R with the respective pneumatic cylinders 82L, 82R so as to expand effectively the variable volumes of the lower chambers of the two cylinders. In this manner, the effective air volume of the cylinder is increased, and air pressure thus will not increase as dramatically when the piston is moved.

Each accumulator 90L, 90R and the respective upper chamber within the pneumatic cylinders 82L, 82R also selectively communicate with the compressed air source (FIG. 5) and with the atmosphere. In the illustrated example, the compressed air source may be, for example, an air compressor, which can be remotely disposed relative to the exercise apparatus. The compressed air source communicates with the upper chambers through a respective inlet valve (shown schematically in FIG. 5). In the illustrated embodiment, the inlet valves for both pneumatic cylinders 82L, 82R are controlled by the left actuator button 66L on the left handgrip 60L when a user manually controls the resistance of the two pneumatic cylinders. The left actuator button 66L is selectably activated by a user to actuate the inlet valves to add air pressure to the lower chamber of each pneumatic cylinder 82L, 82R. The lower chamber is also referred to as the charged side of each cylinder.

The apparatus 10 further includes a control unit enclosure 100 that houses a control system (described below). The control system within the enclosure 100 communicates with an external computer system (FIG. 5) via a communications cable 102 and an adapter unit 104.

The apparatus 10 further includes a control and display panel 110 supported on a riser 112 so that the display panel 110 is positioned in front of a user seated in the seat assembly 22.

Figure 4:
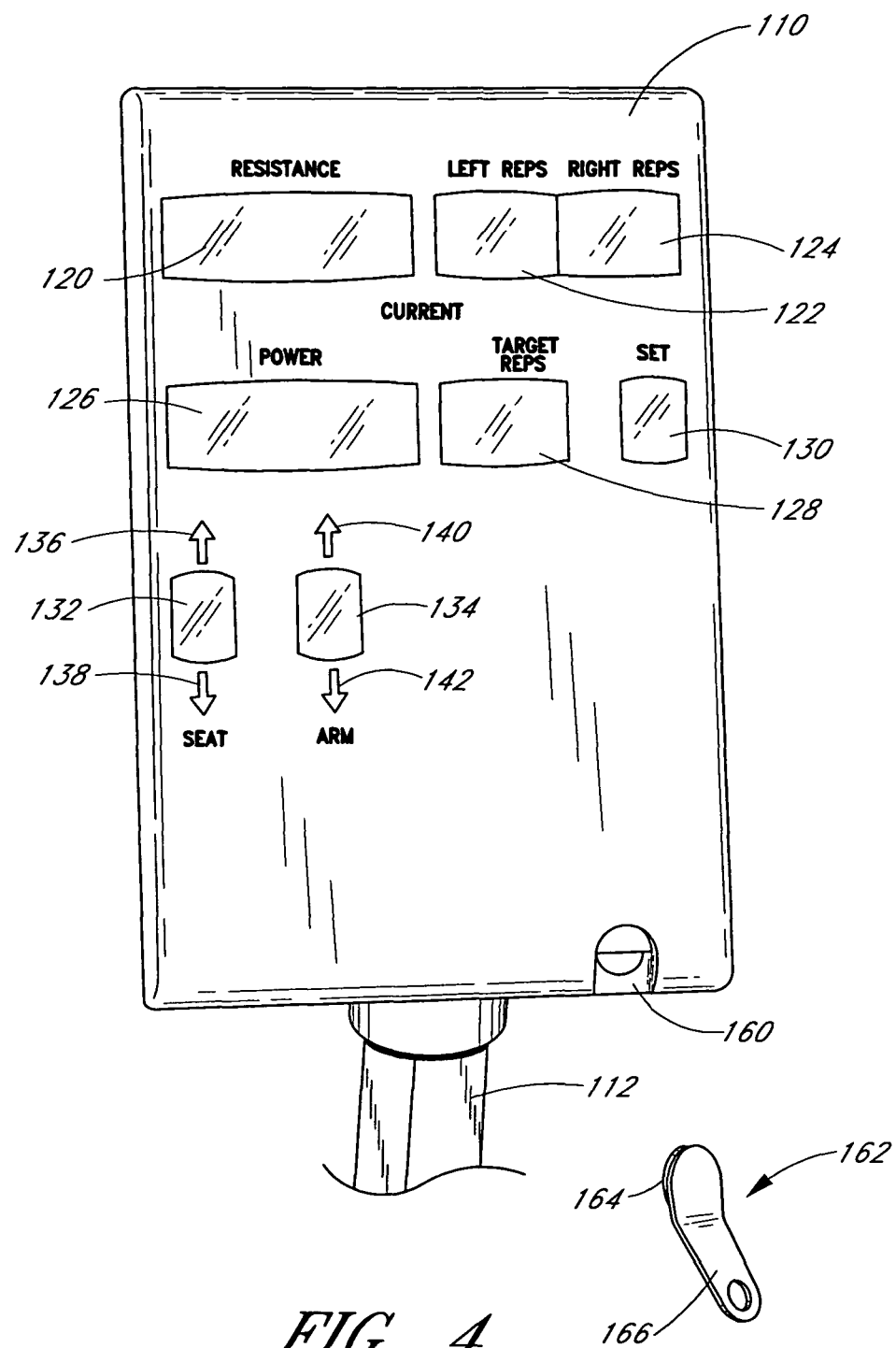
FIG. 4 illustrates a front view of a display panel for the exercise and evaluation apparatus of FIGS. 1, 2 and 3 and the data key that enables the evaluation features in accordance with a preferred embodiment.

As shown in FIG. 4, the display panel comprises a RESISTANCE indicator 120 that displays the total resistance applied to the two handgrips 60L, 60R. The total resistance may be selected by a user by selectively activating the right actuator button 66R to increase the resistance and selectively activating the left actuator button 66L to decrease the resistance. The resistance may also be selected automatically, as described below. The resistance is displayed as the force (in pounds or kilograms) required to move the handgrips 60L, 60R and is calibrated to be equivalent to the force required to move a corresponding stack of conventional weights.

The display unit 110 also advantageously includes a LEFT REPS indicator 122, a RIGHT REPS indicator 124, a POWER indicator 126, a TARGET REPS indicator 128, a SET indicator 130, a SEAT indicator 132, and an ARM indicator 134. A seat up arrow 136 and a seat down arrow 138 are positioned on the display unit 110 proximate the SEAT indicator 132. An arm up arrow 140 and an arm down arrow 142 are positioned proximate the ARM indicator 134. Each up arrow and each down arrow defines the location of a switch beneath the faceplate of the display unit 110. Each switch can be selectively activated by a user pressing on the respective arrow.

The display unit 110 includes a data port recess 160 near the lower right corner of the display unit 110. The data port recess 160 is configured to receive a data key 162. The data key 162 comprises an integrated circuit 164 and a supporting handle 166. The functions of the indicators, the switches, the data port recess and the data key are described in more detail below.

The control unit enclosure 100 is pneumatically connected to the accumulators 90L, 90R and is thus connected to the charged side of the pneumatic cylinders 82L, 82R. The control unit enclosure is also pneumatically connected to a compressed air source (not shown). Within the control unit enclosure 100, a respective inlet valve (shown schematically in FIG. 5, discussed below) for each accumulator 90L, 90R selectively routes compressed air to the accumulator to increase the air pressure in the accumulator and thus increase the air pressure on the charged side of the corresponding pneumatic cylinder. In preferred embodiments, each inlet valve comprises two inlet valves of varying sizes. A larger inlet valve is selectively activated by a control system (described below) to increase the volume of air in the cylinder rapidly when the resistance level of a pneumatic cylinder is increased. A smaller inlet valve is selectively activated by the control system to increase the volume of air in the cylinder in finer increments when the control system is maintaining a selected resistance level.

A respective outlet valve (shown schematically in FIG. 5) for each accumulator is selectively opened to release air to the atmosphere in order to decrease the air pressure on the charged side of the cylinder. In the illustrated embodiment, the outlet valves for both pneumatic cylinders 82L, 82R are controlled by the left actuator button 66L on the left handgrip 60L when a user manually controls the resistance of the two pneumatic cylinders. The left actuator button 66L is selectably activated by a user to actuate the outlet valves to reduce the air pressure to the lower chamber of each pneumatic cylinder 82L, 82R.

A user thus can adjust (e.g., increase or decrease) the air pressure within each resistance assembly by operating the appropriate valves using the right actuator button 66R and the left actuator button 66L.

Although the right actuator button 66R and the left actuator button 66L could be connected directly to the inlet valves and the outlet valves respectively, in the illustrated embodiment it is preferably that the pressure in the left pneumatic cylinder 82L and the pressure in the right pneumatic cylinder 82R be substantially equal so that the resistance applied to the left handgrip 60L and the resistance applied to the right handgrip 60R are substantially equal. In the illustrated embodiment, this is accomplished by providing a respective actuator signal from each actuator button 66R, 66L to a control system 200 (illustrated in a block diagram in FIG. 5) that is located within the control unit enclosure 100. Although represented as a single control system, in the preferred embodiment, the control system 200 comprises a plurality of microprocessors programmed to perform specific functions, such as real-time measurement and adjustment of air pressures, real-time measurement of positions and computation of velocities, communicating with the user via the display panel, and the like.

The control system 200 receives the respective actuator signals and determines whether the user is requesting a pressure increase or a pressure decrease. The control system 200 outputs control signals to a left inlet valve 210L and to a right inlet valve 210R to selectively couple the left accumulator 90L, the right accumulator 90R or both accumulators to a compressed air source 212 to selectively increase the air pressure in one or both accumulators 90L, 90R and the corresponding pneumatic cylinders 82L, 82R. As discussed above, each inlet valve 210L, 210R advantageously comprises a pair of inlet valves. In particular, a large inlet valve in a pair is selectively operated to provide coarse adjustment of the air pressure in the respective pneumatic cylinder. A small inlet valve in a pair is selectively operated to provide fine adjustment of the air pressure in the respective pneumatic cylinder.

The control system 200 outputs control signals to a left outlet valve 214L and to a right outlet valve 214R to selectively release air from one or both accumulators 90L, 90R to selectively decrease the air pressure in the respective pneumatic cylinders 82L, 82R. The inlet valves and the outlet valves are selectively controlled to achieve the desired pressure change while maintaining substantially equal resistances provided by the two pneumatic cylinders 82L, 82R. The control system 200 accomplishes this by receiving a feedback signal from a left pressure transducer 220L coupled to the left pneumatic cylinder 82L and by receiving a feedback signal from a right pressure transducer 220R coupled to the right pneumatic cylinder 82R. The control system 200 samples the feedback signals periodically (e.g., at a sample rate of 10 times per second in a particular embodiment) and compares the pressure measured in the cylinders with the ambient barometric pressure that is also periodically measured using a barometric pressure transducer 224 in order to determine the actual pressure differential applied to each piston. The control system 200 then adjusts the control signals applied to the inlet valves and outlet valves accordingly.

Figure 5:
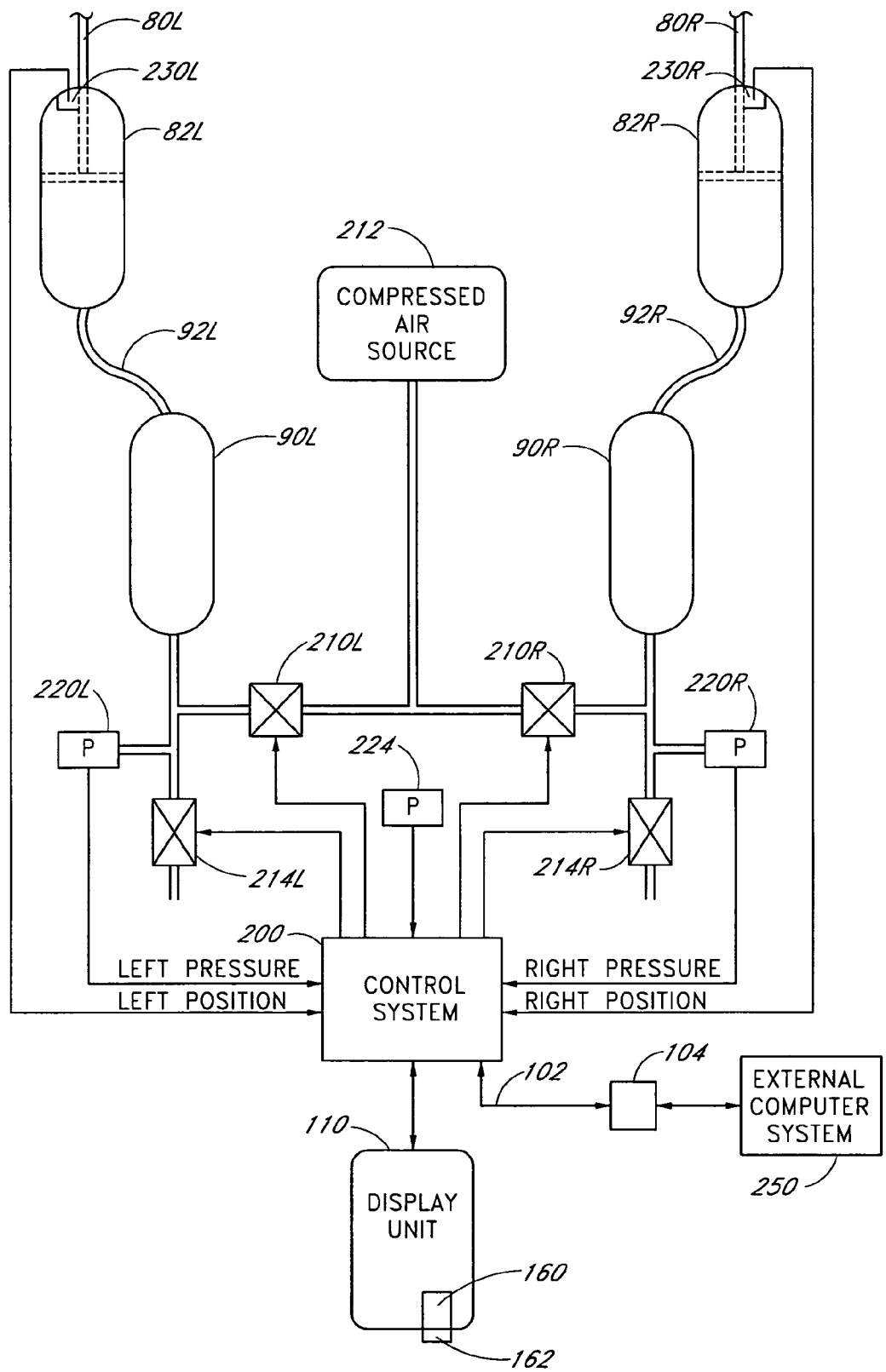
FIG. 5 illustrates a simplified control diagram in accordance with a preferred embodiment.
Figure 6:
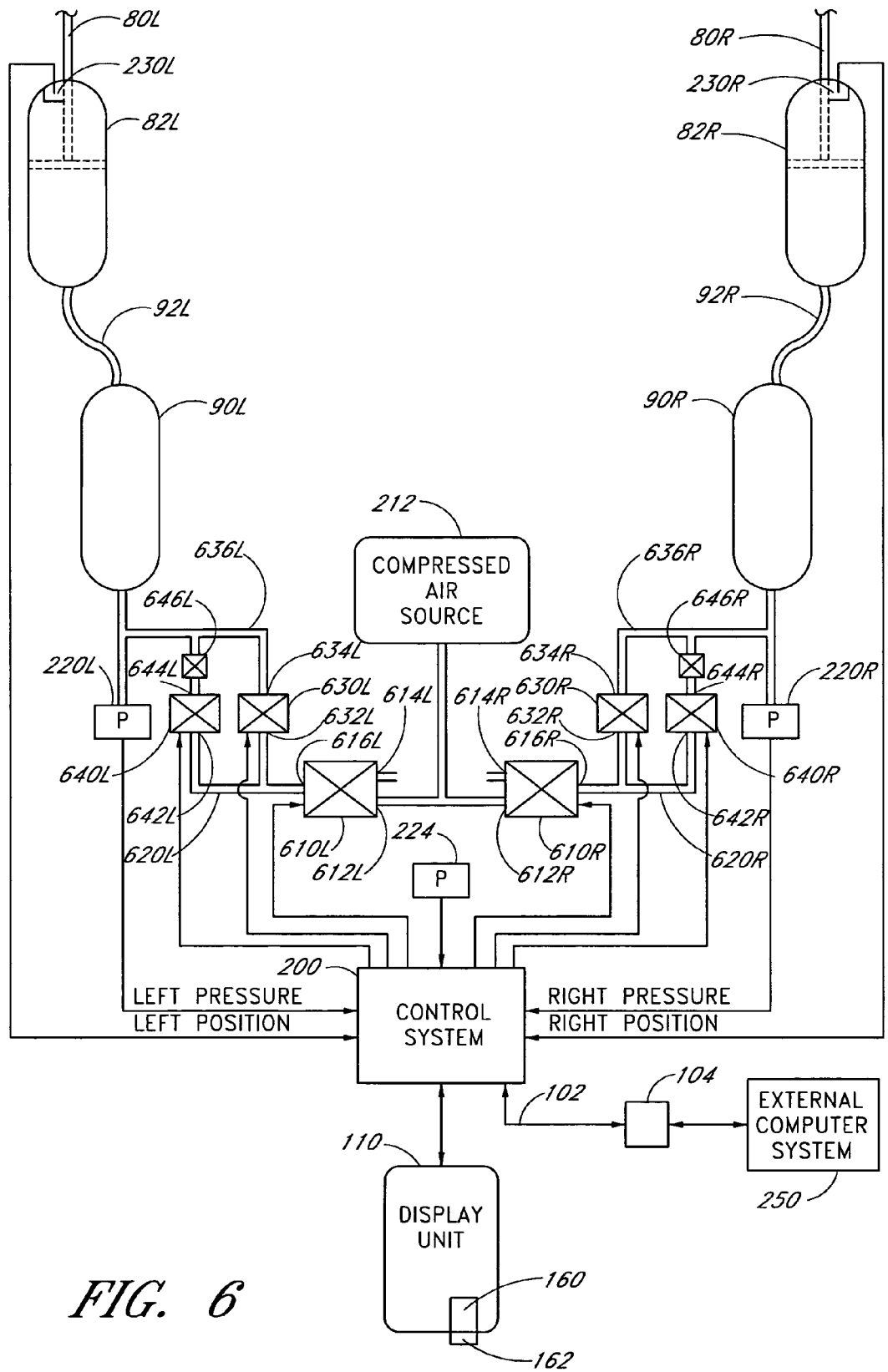
FIG. 6 illustrates a simplified control diagram similar to FIG. 5 but having a different configuration of control valves.

FIG. 6 illustrates a block diagram of a system similar to the system in FIG. 5, in which the control system 200 controls a different configuration for the control valves. The other elements of the block diagram in FIG. 6 are similar to the corresponding elements of the block diagram in FIG. 5 and will not be described in detail in connection with FIG. 6.

In FIG. 6, a first left control valve 610L has a first port 612L coupled to the compressed air source 212. The first left control valve 610L has a second port 614L coupled to the atmosphere. The first left control valve 610L has a third port 616L coupled to a left common galley 620L. The first left control valve 610L is controlled by the control system 200 to be in one of two modes. In a first mode, the first port 612L is coupled to the third port 616L so that the left common galley 620L is coupled to the compressed air source 212. In the second mode, the second port 614L is coupled to the third port 616L so that the left common galley 620L is coupled to the atmosphere.

The left common galley 620L is coupled to a first port 632L of second left control valve 630L and to a first port 642L of a third left control valve 640L. A second port 634L of the second left control valve 630L is coupled to the left accumulator 90L and to the left pressure transducer 220L via a pneumatic tube 636L. A second port 644L of the third left control valve 640L is coupled to the pneumatic tube 636L via an adjustable orifice 646L. Although shown as a separate element, the adjustable orifice 646L may advantageously be included as part of the third control valve 640L.

The second left control valve 630L and the third left control valve 640L are controlled by the control system 200. The second left control valve 630L operates as a high flow valve. The control system 200 activates the second left control valve 630L to make course adjustments to the volume of air in the accumulator 90L and the pneumatic cylinder 82L. The third left control valve 640L operates as a low flow valve. The control system 200 activates the second left control valve 630L to make fine adjustments to the volume of air in the accumulator 90L and the pneumatic cylinder 82L in accordance with the flow rate determined by the adjustable orifice 640L.

The control system 200 operates the first left control valve 610L in combination with the second left control valve 630L and the third left control valve 640L. The mode of the first left control valve 610L determines whether the volume of air in the left accumulator 90L and the left pneumatic cylinder 82L is being increased or decreased and the selective activation of the second left control valve 630L or the third left control valve 640L determines a rate at which the increase or decrease in volume occurs.

Similarly, a first right control valve 610R has a first port 612R coupled to the compressed air source 212, a second port 614R coupled to the atmosphere, and a third port 616R coupled to a right common galley 620R. The first right control valve 610R is controlled by the control system 200 to be in one of two modes as described above for the first left control valve 610L.

The volume of air in the right accumulator 90R and the right pneumatic cylinder are controlled by a second right control valve 630R having a first port 632R and a second port 634R and third right control valve 642R having a first port 642R, a second port 644R and an adjustable orifice 646R. The right accumulator 90R and the right pressure transducer 220R are coupled to the second port 634R of the second right control valve 630R and to the adjustable orifice 646R by a pneumatic tube 636R.

The second right control valve 630R and the third right control valve 640R are controlled by the control system 200 in combination with the first right control valve 610R to make course adjustments and fine adjustments to the volume of air in the accumulator 90R and the pneumatic cylinder 82R as discussed above for the corresponding left components.

The control system 200 uses the pressure measurements to calculate the resistive force that will be perceived by a user when the handgrips are moved. The calculated resistive force is advantageously displayed as the resistance on the RESISTANCE indicator 120 of the display unit 110 so that a seated user can readily observe the resistance selected by using the left actuator button 66L and the right actuator button 66R. As discussed above, the resistance is displayed as the force (in pounds, kilograms or newtons) required to move the handgrips 60L, 60R and is calibrated to be equivalent to the force required to move a corresponding stack of conventional weights.

Once the pressures in the pneumatic cylinders are established by the control system 200, the user can apply force to the left handgrip 60L and apply force to the right handgrip 60R to move the handgrips forward. The forward movement of the handgrips is coupled via the pivoting action of the left lever 40L and the right lever 40R about the left hinge 32L and the right hinge 32R to cause the left connecting rod 80L and the right connecting rod 80R to move within the left pneumatic cylinder 82L and the right pneumatic cylinder 82R. As discussed in U.S. Pat. No. 4,257,593, incorporated by reference herein, the air within the pneumatic cylinders 82L, 82R and the accumulators 90L, 90R is compressed as the pistons move within the cylinders. The force required to compress the air is coupled through the levers to oppose the movement of the handgrips to provide the user with the effect of lifting weights against gravity but without the inertial effects of conventional weights. It will be appreciated that as the pistons move farther into the respective cylinders, the force required to further compress the air increases; however, the shapes of the upper lever portions 44L, 44R are selected such that the user is provided with increasingly more leverage to compensate for the increased air pressure. Thus, the user pushes against substantially the same force throughout each exercise stroke.

In addition to the mechanical control of the force provided by the shapes of the upper lever portions 44L, 44R, the force is also controlled by the control system 200, which continues to sample the pressure transducers (e.g., at 10 times per second) throughout each exercise stroke and selectively applies control signals to the inlet valves and the outlet valves to maintain the correct pressure in each pneumatic cylinder throughout the exercise stroke. Since the pressure is intended to vary throughout the exercise stroke, the control system 200 must also determine the position of each cylinder throughout the stroke. This is accomplished in the preferred embodiment by precisely measuring the position of each cylinder. In particular, the position of the piston within the left pneumatic cylinder 82L is determined by a left position transducer 230L, and the position of the piston within the right pneumatic cylinder 82R is determined by a right position transducer 230R. In the illustrated embodiment, each of the position transducers 230L, 230R is implemented by a resistive position transducer having a resolution of 1 part in 16,000,000 and having a linearity of better than 1 percent. Each position transducer 230L, 230R is sampled 400 times per second to determine the instantaneous position of the piston.

The control system 200 uses the measured positions of each piston to determine the instantaneous volume of the air in each cylinder. The control system 200 uses the measured barometric pressure and the measured pressures in each cylinder as inputs and solves the universal gas law equation ten times per second to determine whether to add or remove air from each cylinder to maintain the desired resistance at each position in the exercise stroke. The control system 200 also measures the supply pressure provided by the compressor (not shown) via a storage accumulator (not shown) to determine the amount of time to open a respective air inlet valve in order to add the proper amount of air to a cylinder.

Although the apparatus 10 can be used for exercising the muscles to increase the performance of the muscles, the apparatus 10 is particularly advantageous for implementing the system and method in accordance with aspects of the present invention. In particular, the ability of the control system 200 to accurately measure pressure in the pneumatic cylinders and to accurately measure the position of the pistons within the pneumatic cylinders enables the apparatus 10 to determine the velocity of movement against the resistive force throughout an exercise stroke and to thereby determine the power of the user throughout an exercise stroke. As described below, by performing a series of such measurements over a range of resistance forces, the user's power as a function of force can be determined. Armed with the information regarding the user's power capabilities, a trainer, a therapist, or the user can tailor exercises to the user's capabilities and the user's goals.

As discussed above, it is possible to determine average power produced by a muscle or a group of muscles by measuring the distance a force is moved, by measuring the time required to move the force over the measured distance and by measuring or knowing the amount of force being moved. However, such a measurement only provides an average power for an exercise stroke and does not provide any details regarding maximum power during the exercise stroke and does not provide other useful information described below in connection with embodiments in accordance with aspects of the present invention.

In addition to providing the basic control functions described above to enable the apparatus 10 to be used as an exercise device, the control system 200 is advantageously programmed to enable the apparatus 10 to be used as an evaluation tool.

As discussed above, the right actuator button 66R is selectively activated to increase the resistance to the movement of the left handgrip 60L and the right handgrip 60R, and the left actuator button 66L is selectively activated to decrease the resistance to the movement of the two handgrips. Thus, a user is able to increase or decrease the effective "weight" used in an exercise without moving from the seat assembly 22. When the apparatus 10 is used as an evaluation tool, the left actuator button 66L and the right actuator button 66R are activated at the same time by a user in the preferred embodiment. Since there is no reason for a user to attempt to increase the resistance and decrease the resistance at the same time, the concurrent activation of both buttons should not occur during conventional exercise routines. Thus, when the control system 200 receives concurrent signals from both buttons, the control system 200 enters an evaluation routine to perform one embodiment of a method in accordance with one aspect of the present invention. It should be understood that the control system 200 can be caused to initiate and perform the evaluation routine by other means, such as, for example, by activation of a switch dedicated to controlling the operation modes of the control system 200. For example, the switch may be selectively activated by a key.

As a failsafe measure, the control system 200 is advantageously programmed to enter the evaluation routine only when the apparatus 10 is activated by an authorized user by applying the data key 162 to the data port recess 160 of the display unit 110 (FIG. 4). The data port recess 160 defines the location of an interface that communicates with the integrated circuit 164 on the data key 162. In one embodiment, the integrated circuit 164 on the data key 162 comprises an iButton® data device available from Maxim/Dallas Semiconductor Corporation. A compatible interface, also available from Maxim/Dallas Semiconductor Corporation, is positioned in the data port recess 160 of the display unit 110 to communicate with the integrated circuit 164 when the data key 162 is present. A non-volatile memory within the integrated circuit 164 stores user identification information and advantageously includes historical information related to the user.

The integrated circuit 164 advantageously includes data specific to each of the apparatuses in a training facility such that when the user applies the data key 162 to the data port recess 160 of a particular apparatus, the data are transferred to the apparatus to cause the apparatus to automatically adjust settings (e.g., resistance levels) and display other settings (e.g., seat and lever arm adjustments) that were last used by the particular user on the particular apparatus. For example, the SEAT indicator 132 is activated by the control system 200 to show a single-digit value corresponding to a conventional height adjustment number proximate the seat bottom portion 26. Similarly, the ARM indicator 134 is activated by the control system 200 to show a single-digit value corresponding to a selected one of the holes 52L, 52R in the arm adjustment selectors 50L, 50R that the user has previously determined to be the most suitable. If the user has not previously used a particular apparatus 10, the two displays may be advantageously initialized to a predetermined value or may be caused to blink to indicate to the user that a value needs to be entered. The user selectively presses on the seat up arrow 136 or the seat down arrow 138 to increment or decrement the associated numerical indication to correspond to the current setting of the seat bottom portion. Similarly, the user selectively presses on the arm up arrow 140 or the arm down arrow 142 to increment or decrement the associated numerical indication to correspond to the current setting of the arm adjustment selectors SOL, 50R. Changes to the numerical indications are stored in the integrated circuit 164 in association with the particular apparatus 10 so that when the user removes the data key 162, the settings are saved in the integrated circuit 164 and will be displayed to remind the user of the settings the next time the user activates the apparatus 10 by applying the data key 162 to the data port recess 160.

In accordance with the method of evaluation described herein, the integrated circuit 164 of the data key 162 identifies the user, and the control system 200 confirms that the user is authorized to perform the evaluation method. Thus, when the user activates both buttons 66L, 66R, the control system 200 enters the evaluation method and operates the apparatus 10 in the manner described below in order to obtain data that is processed to evaluate the user's power.

As further illustrated in FIGS. 5 and 6, the control system 200 is selectively coupled via the communications cable 102 and the adapter 104 to an external computer system 250. The connection to the external computer system 250 may be a point-to-point connection as illustrated in FIGS. 5 and 6 or the connection may be through a network (hardwired or wireless) wherein the control system 200 is coupled to the network via the adapter 102 and the external computer system 250 is also coupled to the network.

Figure 7:
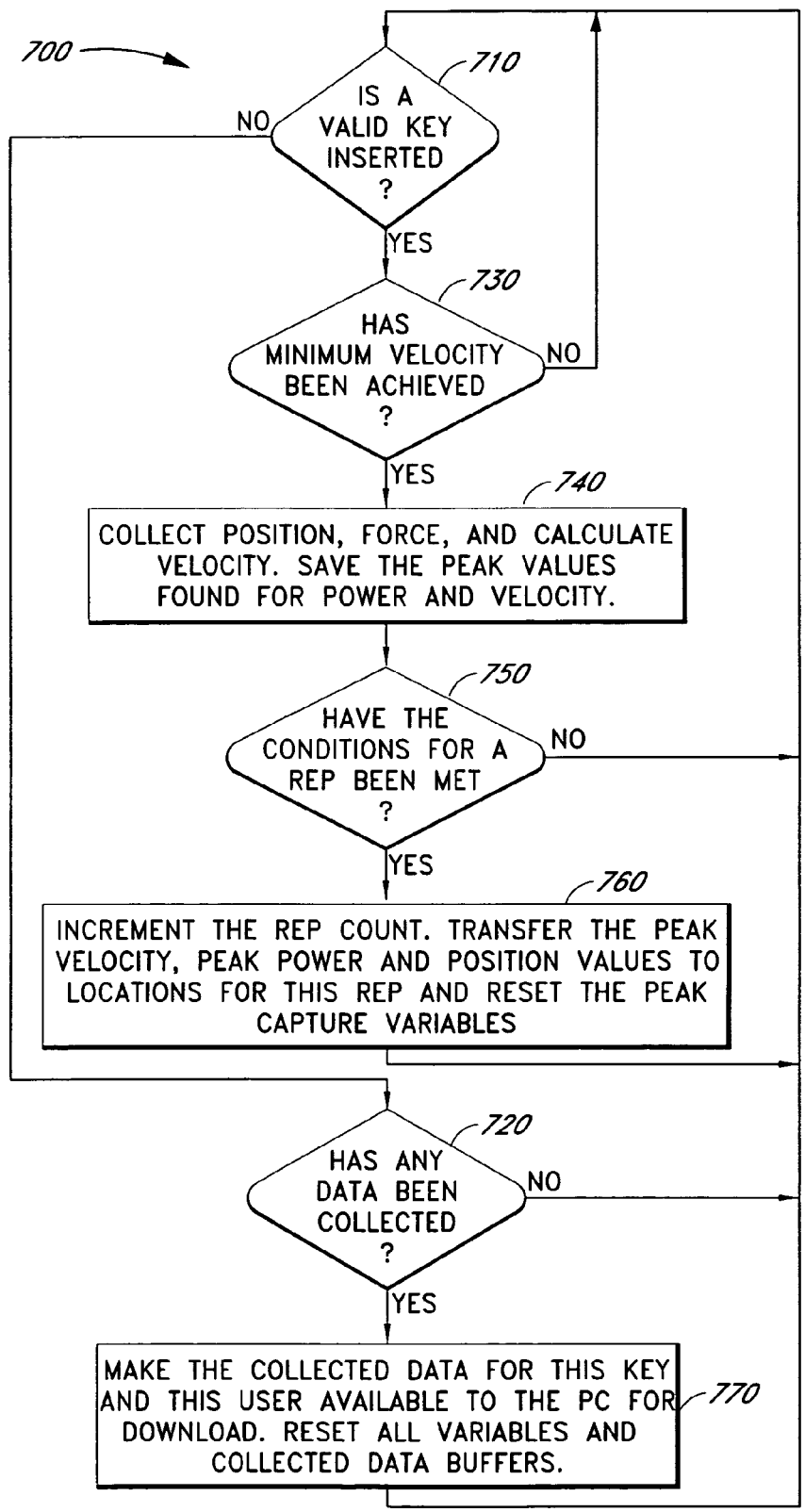
FIG. 7 illustrates a flow chart of a data gathering routine in accordance with a preferred embodiment.
Figure 8:
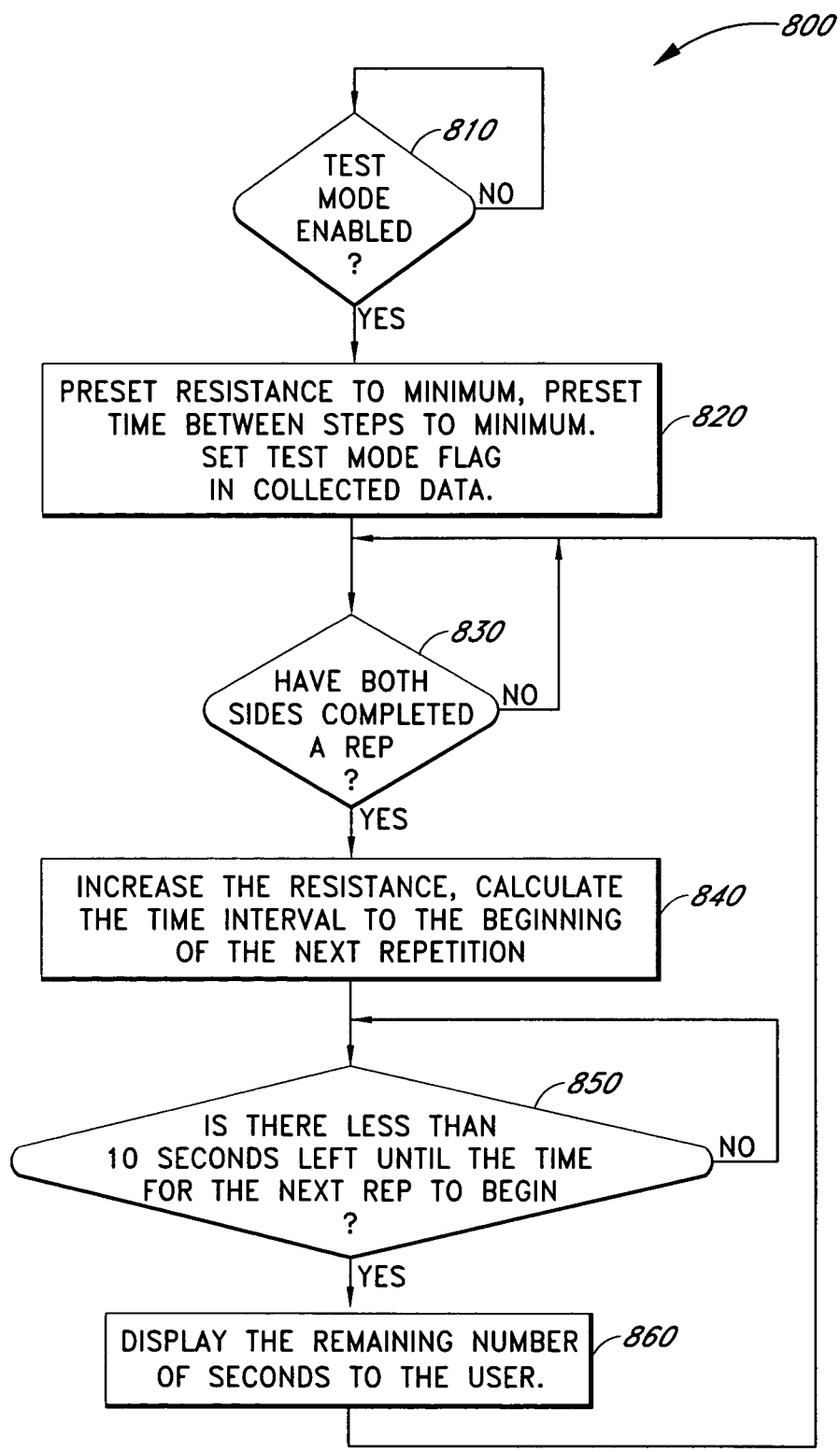
FIG. 8 illustrates a flow chart of a power evaluation routine in accordance with a preferred embodiment.

Routines performed by the control system 200 in accordance with embodiments of the present invention are illustrated in FIGS. 7 and 8. In particular, FIG. 7 illustrates a data gathering routine 700 that is performed repeatedly by the control system as long as power is provided to the apparatus 10. For example, in a preferred embodiment, the data gathering routine 700 is performed at a rate of 400 times per second (i.e., every 2.5 milliseconds). In alternative embodiments, the rate can be increased to increase the number of data samples collected during each exercise stroke and thereby increase the resolution of the data or the rate can be decreased to reduce requirements for processing speed and data storage. The preferred rate has been determined to provide adequate data resolution with reasonable requirements for processing speed and data storage. The rate can be determined by a timer coupled to an interrupt system to cause the control system 200 to start the data gathering routine at the beginning of every 2.5-millisecond interval.

The data gathering routine 700 first enters a decision block 710 wherein the control system 200 interrogates the interface within the data port recess 160 of the display unit 110 to determine whether a valid data key 162 (e.g., a data key having identification information that identifies an authorized user of the apparatus 10) is positioned in the data port recess 160. If a data key is not present, the data gathering routine advances to a decision block 720, wherein the routine determines whether any data were collected while a data key was positioned in the data port recess 160. For example, the routine examines a data buffer within the control system 200 and determines whether the data buffer is empty. If the data buffer is empty and no data has been collected, the control system returns to the beginning of the routine and waits until the beginning of the next 2.5 millisecond interval before repeating the steps in the decision blocks 710 and 720. If the data buffer is not empty, then data were collected while the key was inserted, and the collected data need to be transferred in order to clear the data buffer for the next time the apparatus 10 is used. The data transfer is discussed below.

If the data collecting routine 700 determines in the decision block 710 that a valid data key is present in the data port recess 160, the routine advances to a decision block 730 and obtains the velocities of the pistons within the pneumatic cylinders 82L, 82R. The velocities are advantageously calculated by determining the differences between the current outputs of the position transducers 230L, 230R with the previous outputs of the position transducers to determine the amounts of movement during the interval between samples. The calculated velocity for each piston is compared to a minimum velocity to determine whether the user is moving the handgrips at a sufficient rate to indicate that an exercise stroke is in progress.

If the data collecting routine 700 determines that the minimum velocity has not been achieved by at least one of the pistons, the control system returns to the beginning of the routine and waits until the beginning of the next 2.5 millisecond interval before repeating the step in the decision block 710. If the data key remains inserted, the routine will again advance to the decision block 730 and compare the velocities of the pistons to the minimum velocity.

If, in the decision block 730, the data collecting routine 700 determines that a minimum velocity has been achieved by at least one of the pistons, the routine advances to a data gathering procedure 740 wherein the current positions and the current force are collected and saved for the pistons in the two cylinders. The velocities for the two cylinders are calculated and saved. The current powers being generated by the two pistons (i.e., force×velocity) are also calculated and saved. In addition, during each sample, the control system 200 determines independently for each piston whether the current calculated velocity for the piston is greater than a previously calculated highest velocity for the piston during the current exercise stroke. If so, the newly calculated velocity is saved as the new peak velocity for the piston. A similar determination is made for the current calculated power for each piston, and a new peak power is saved for a piston if the current calculated power for that piston is greater than the previously saved peak power for that piston.

After saving the current data and selectively updating the peak velocities and the peak powers in the procedure 740, the data collecting routine 700 advances to a decision block 750 wherein the control system 200 determines whether the conditions for a complete repetition have been met. For example, the control system may determine from the outputs of the position transducers whether the positions of the pistons are continuing to increase. If the position of at least one of the pistons is continuing to increase, the control system returns to the beginning of the routine and waits until the beginning of the next 2.5 millisecond interval before repeating the steps beginning with the decision block 710.

If, in the decision block 750, the positions of both cylinders are no longer increasing (e.g., the pistons are stationary or the pistons are moving in the opposite direction), the data collecting routine 700 advances to a procedure 760 wherein the control system 200 increments the repetition counter and displays the current repetition counts on the LEFT REPS display 122 and the RIGHT REPS display 124. The control system transfers the calculated peak velocity, the calculated peak power and the position values (e.g., the positions measured at each sample time) to respective storage locations in a buffer associated with the particular repetition count. Thereafter, the control system resets the peak velocity and the peak power for each piston. The control system returns to the beginning of the routine and waits until the beginning of the next 2.5 millisecond interval before repeating the steps beginning with the decision block 710.

If, in the decision block 720, the data collecting routine 700 determines that data were collected while a valid data key 162 was positioned in the data port recess 160, then the control system 200 advances to a procedure 770 wherein the data collected while the data key was present are transferred to a download buffer (not shown). The data in the download buffer are available to be downloaded by the external computer system 250. In particular, the collected data are stored in association with the identification information on the data key 162 so that when the data are downloaded to the external computer system 250, the data are readily determined to be data produced by a user to whom the data key 162 is assigned. In addition, the procedure 770 resets all the variables (e.g., the repetition counters, the peak velocity, the peak power) and clears the data collection buffers.

After the data are transferred to the download buffer and the variables are reset, the data collecting routine 700 returns to the beginning of the routine and waits until the beginning of the next 2.5 millisecond interval before repeating the steps described above. Since the data key 162 has been removed, the transfer of the collected data and the resetting of the variables places the apparatus 10 in condition for the next user to apply a respective data key 162. Alternatively, the current user may re-insert his or her data key 162 in order to collect additional data.

The data collecting routine 700 illustrated in FIG. 7 runs as an independent thread in the control system 200 and continues to sample the presence of the key. If the key is present, the routine continues to sample and collect data in the manner described above regardless of whether a user is using the apparatus 10 for exercise or a user is being evaluated, as described below.

FIG. 8 illustrates a power evaluation routine 800 that enables the apparatus 10 to be used to determine the maximum power generated by a user and to determine the force and velocity at which the maximum power is generated. The routine 800 operates as an independent thread on the control system 200 and automatically increases the resistance applied to the handgrips 60L, 60R of the apparatus in a predetermined sequence and at predetermined time intervals in order to perform the evaluation procedure. While the steps in the power evaluation routine 800 are being performed, the above-described data collecting routine 700 continues to run independently to collect the data generated as the user operates the apparatus 10 in response to the changes in resistance imposed by the power evaluation routine 800.

The power evaluation routine 800 begins with a decision block 810 in which the control system 200 inputs the signals from the left actuator button 66L and the right actuator button 66R to determine whether a user has activated the left actuator button 66L and the right actuator button 66R at the same time. The concurrent activation of both actuator buttons 66L, 66R does not increase the resistance provided by either the left pneumatic cylinder 82L or the right pneumatic cylinder 82R. Rather, the concurrent activation of both actuator buttons signals the control system 200 that the user wants to initiate the power evaluation mode of the apparatus 10.

If, in the decision block 810, the control system 200 determines that at least one of the actuator buttons 66L, 66R is not actuated, the power evaluation routine 800 returns to the beginning and enters the decision block 810 again. The control system repeats the decision process in the decision block 810 until the user activates both actuator buttons at the same time.

When both actuator buttons 66L, 66R are activated at the same time, the power evaluation routine 800 advances to a evaluation initialization procedure 820 wherein the control system 200 presets the resistance of each pneumatic cylinder 82L, 82R to a preset initial resistance. For example, the initial resistance may be preset to 2.5 pounds per pneumatic cylinder to provide a total resistance of 5 pounds for both cylinders. Alternatively, the initial resistance may be set to a significantly larger value. For example, when evaluating the power of trained athlete, such as a power lifter or a shot putter, the initial resistance may be set to 20 pounds or more.

In the evaluation initialization procedure 820, the control system 200 also presets the time between repetitions to a minimum time interval. For example, the minimum time interval may be 10 seconds or less. In addition, the control system sets a test mode flag within the data buffer into which the collected data are stored by the data collecting routine 700. For example, the test mode flag is advantageously a particular storage location within the data buffer that is evaluated by the external computer system 250, as described below in connection with FIG. 10.

As the control system 200 is performing the evaluation initialization procedure 820 in the power evaluation routine 800, the control system advantageously blinks the LEFT REPS display 122 and the RIGHT REPS display 124 as an indication to the user that the user should wait before pushing on the handgrips. After the evaluation initialization procedure 820 is completed, the control system discontinues blinking the two displays and outputs signals to display the values of the repetition counters, which were set to 0 by the data collecting routine 700 in response to the removal of the data key 162 by the previous user.

When the LEFT REPS display 122 and the RIGHT REPS display 124 stop blinking with values of 0 displayed on each display, the user applies maximum force to the handgrips 60L, 60R to move the handgrips at the maximum speed the user can achieve. The low inertia provided by each of the pneumatic cylinders 82L, 82R enables the user to reach a high speed quickly. The low inertia also enables the user to maintain a high speed throughout the exercise stroke since the user does not have to worry about the inertia of a conventional weight stack continuing to pull the user's arms forward even after the user stops applying force. The user continues to push the handgrips forward to the limit of the user's reach. The user then pulls the handgrips back to the initial starting positions of each handgrip. As discussed above, when the decision block 760 in the data collecting routine 700 detects the completion of the repetitions by both handgrips, the procedure 720 increments the repetition counters accordingly.

After presetting the initial resistance and the minimum time interval in the procedure 820, the power evaluation routine 800 advances to a decision block 830 wherein the control system 200 monitors the repetition counters to determine whether the repetition counters have been incremented by the data collecting routine 700, as described above. Since the two handgrips 60L, 60R are operated independently, the user may not complete the exercise stroke at the same time for both handgrips. If at least one of the left repetition counter or the right repetition counter has not been incremented, the power evaluation procedure returns to the decision block 830 and continues to monitor the two repetition counters.

When the power evaluation procedure 800 determines in the decision block 830 that both the left repetition counter and the right repetition counter have been incremented by the procedure 760 in the data collecting routine 700, the power evaluation routine advances to an update procedure 840. In the update procedure 840, the control system 200 outputs commands to the left control valves 610L, 630L, 640L and outputs commands to the right control valves 610R, 630R, 640R while monitoring the left pressure transducer 220L and the right pressure transducer 220R. The volumes of air in the pneumatic cylinders 82L, 82R and the respective accumulators 90L, 90R are selectively increased or decreased to cause the resistances of each pneumatic cylinder 82L, 82R to be increased to the next incremental resistance level. The increments can be selected in accordance with the strength of users. For example, in an embodiment intended to evaluate non-athletic users, the total resistance level provided by both pneumatic cylinders may be increased in 5-pound increments. The resistance level may be increased by incremental amounts less than 5 pounds for weak users (e.g., users in rehabilitation). For athletic users, the resistance level may be advantageously increased by larger amounts, such as, for example, 20-pound increments. Other increments between 5 pounds and 20 pounds and increments greater than 20 pounds can also be used for particular applications. For example, as discussed below, the amount of the increments can be selected in accordance with a desired maximum resistance level and a desired number of strokes to reach the maximum resistance level.

The initial force and the amount by which the force is incremented are advantageously selected to increase the force to a level where the user can no longer complete twenty exercise strokes. Thus, in the two examples, the non-athletic user may be expected to not be able to complete a twentieth repetition at approximately 100 pounds, and the athletic user may be expected to not be able to complete a repetition at 400 pounds. In one particularly advantageous embodiment, the user is provided with an initial starting force and the decrease in velocity in response to the first few (e.g., four) increments of force are used to predict the likely maximum force the user can move. The subsequent increments of the force are selected to exceed the likely maximum force for the user at approximately 20 repetitions. Twenty repetitions are advantageously selected in the illustrate embodiment to provide a sufficient number of data points within a reasonable amount of time to complete the evaluation procedure.

In other embodiments, the maximum resistance force can be set by the user using the left actuator button 66L or the right actuator button 66R. For example, the maximum resistance may be entered when the apparatus is being used to periodically test an athlete who established his or her maximum resistance capability in one or more previous evaluation sessions or by using other equipment. In such embodiments, the incremental increases in resistance may be calculated in accordance with a predetermined number of exercise strokes (e.g., 20) to reach the maximum resistance entered by the user. In a further modification of such an embodiment, the user is prompted to enter a number of exercise strokes desired to reach the maximum resistance previously entered. For example, this modification enables a user to enter a smaller number of exercise strokes in order to more quickly test for improvements in power in comparison to previous evaluation sessions. This modification is advantageous when a large number of users need to be periodically evaluated (e.g., the players on a football team, a baseball team, or the like) and it is desirable to evaluate each user quickly.

In another modification, the user is prompted to enter an initial resistance force and to then enter an incremental resistance force. This modification enables the user to focus the evaluation session on resistance forces in a range where the user is seeking to improve his or her power generation. For example, a baseball player may concentrate on developing more power in a lower range of forces, a shot putter may concentrate on developing higher speeds at a mid-range of forces, and a power lifter may concentrate on developing more power at a higher range of forces. In each case, the user attempts to achieve greater velocities while moving against the resistances in the selected range of forces.

In addition to incrementing the force to the next level in the procedure 840, the control system 200 also calculates a time interval before the start of the next repetition. At the lower resistance levels, a user's muscles do not require much rest after an exercise stroke before being ready to perform the next exercise stroke at the next higher resistance level. As the resistance level increases, the amount of energy expended during each exercise stroke becomes larger. In addition, the cumulative energy expended in each exercise stroke increases at a higher rate. The procedure 840 provides an increasing time interval between exercise strokes to provide more recovery time for the user's muscles between exercise strokes to provide a more accurate indication of the user's performance at the higher resistance levels.

After setting the time interval in the procedure 840, the power evaluation routine 800 advances to a decision block 850 wherein the control system 200 determines whether there is less than 10 seconds remaining in the time interval. If more than 10 seconds remain, the power evaluation routine returns to the decision block 850 and continues to evaluate the time remaining in the time interval.

When the power evaluation routine 800 determines in the decision block 850 that less than 10 seconds are remaining in the time interval, the power evaluation routine advances to a procedure 860 wherein the control system 200 displays the seconds remaining in the interval on the SET display 130 on the display unit 110. The control system continues to display the remaining seconds in the time interval as the seconds decrement to 0. When the seconds decrement to 0, the power evaluation routine returns to the decision block 830 and waits for the user to complete an exercise repetition against the increased resistance.

The power evaluation routine 800 repeats the operations in the decision block 830, the procedure 840, the decision block 850 and the procedure 860 as long as the data key 162 is positioned in the data port recess 160. At the same time, the data collecting routine 700, operating as an independent thread, continues to collect data as the user performs the exercise strokes. When the user is no longer able to complete an exercise stroke after the resistance is increased, the user removes the data key 162 to conclude the data collecting process performed by the data collecting routine 700. In addition, removal of the data key 162 causes the control system 200 to terminate the current power evaluation routine 800 and return to the decision block 810 at the beginning of the power evaluation routine 800 to wait for both actuators 66R, 66L to be concurrently activated to start a new power evaluation routine. In other advantageous embodiments, the data collecting process concludes when the data collecting routine 700 determines that a sufficient amount of data has been collected to evaluate the user's power regardless of whether the user is able to complete more exercise strokes or exercise strokes at greater resistance values. For example, as discussed above, the data collecting process can be advantageously concluded when the user has performed a predetermined number of exercise strokes or when the resistance has been incremented to a predetermined resistance level.

As discussed above, as the exercise stroke is occurring, the control system 200 continues to monitor the pressures within the pneumatic cylinders 82L, 82R and adjusts the pressures as required to maintain the selected force on the handgrips close to the desired force throughout the exercise stroke.

In a variation of the above-described power evaluation routine 800, the procedure 860 is advantageously modified to provide the user with only a single indication to start an exercise stroke. By not providing a countdown or other warning prior to the next exercise stroke, the control system 200 can determine a user's reaction time by measuring the time from the appearance of the indication to the initial movement of the exercise stroke.

As discussed above, after the data key 162 is removed, the data collecting routine 700 transfers the collected data to a buffer that is accessible by the external computer system 250. For example, the control system 200 advantageously includes a network interface that couples to a network via the cable 102 and the adapter 104 in order to communicate with the external computer system 250, which is also coupled to the network.

Figure 9:
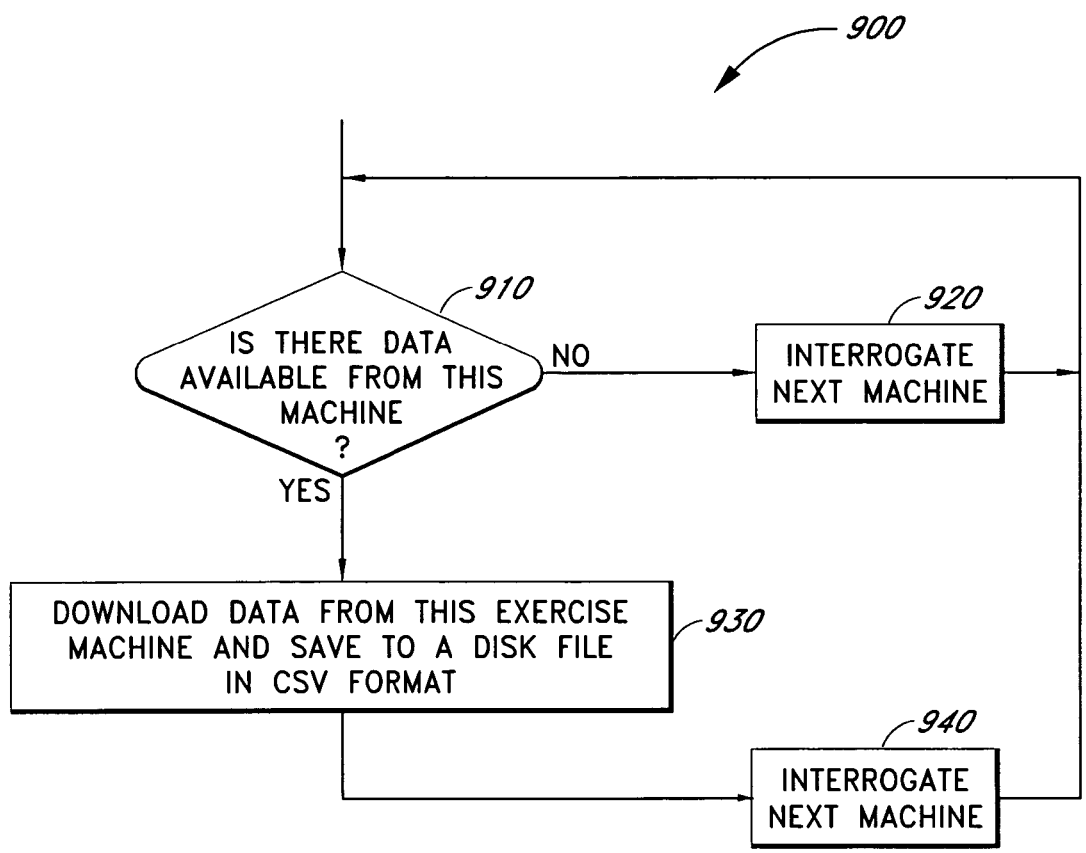
FIG. 9 illustrates a flow chart of a polling routine for downloading data from a plurality of exercise machines.

As illustrated by a polling routine in FIG. 9, the external computer system 250 systematically interrogates each apparatus 10 connected to the common network. In particular, in a decision block 910 the external computer system 250 evaluates the response received from a first apparatus 10 on the network and determines whether the response indicates that the apparatus 10 has data available. As discussed above, the apparatus 10 indicates whether collected data were transferred to the transfer buffer by the procedure 770 in FIG. 7 that have not yet been transferred (i.e., downloaded) to the external computer system 250 in response to a prior interrogation. If no data are available to be transferred, the external computer system addresses and interrogates the next apparatus 10 on the network in a procedure 920 and then returns to the decision block 910 to determine whether data are available from the next apparatus to be downloaded.

If the external computer system determines in the decision block 910 that data are available to be downloaded from the currently addressed apparatus 10, the external computer system 250 advances to a procedure 930 wherein the external computer system 250 downloads the collected data from the apparatus 10 and saves the collected data in a disk file. For example, in the illustrated embodiment, the collected data are saved in a comma separated value (CSV) format, which is a data exchange format that is compatible with many spreadsheet programs and other data evaluation programs. After storing the data downloaded from a currently addressed apparatus, the external computer system addresses and interrogates the next apparatus 10 in a procedure 940 and then returns to the decision block 910 to determine whether data are available from the next apparatus to be downloaded.

The routine 900 illustrated in FIG. 9 is advantageous for an exercise or evaluation facility having a large number of apparatuses that collect data as users perform exercise routines or as users are evaluated. The external computer system stores the collected data in association with the identification information from the data key 162 that enabled the collection of the data so that the data can later be identified as being generated by a particular user.

Figure 10:
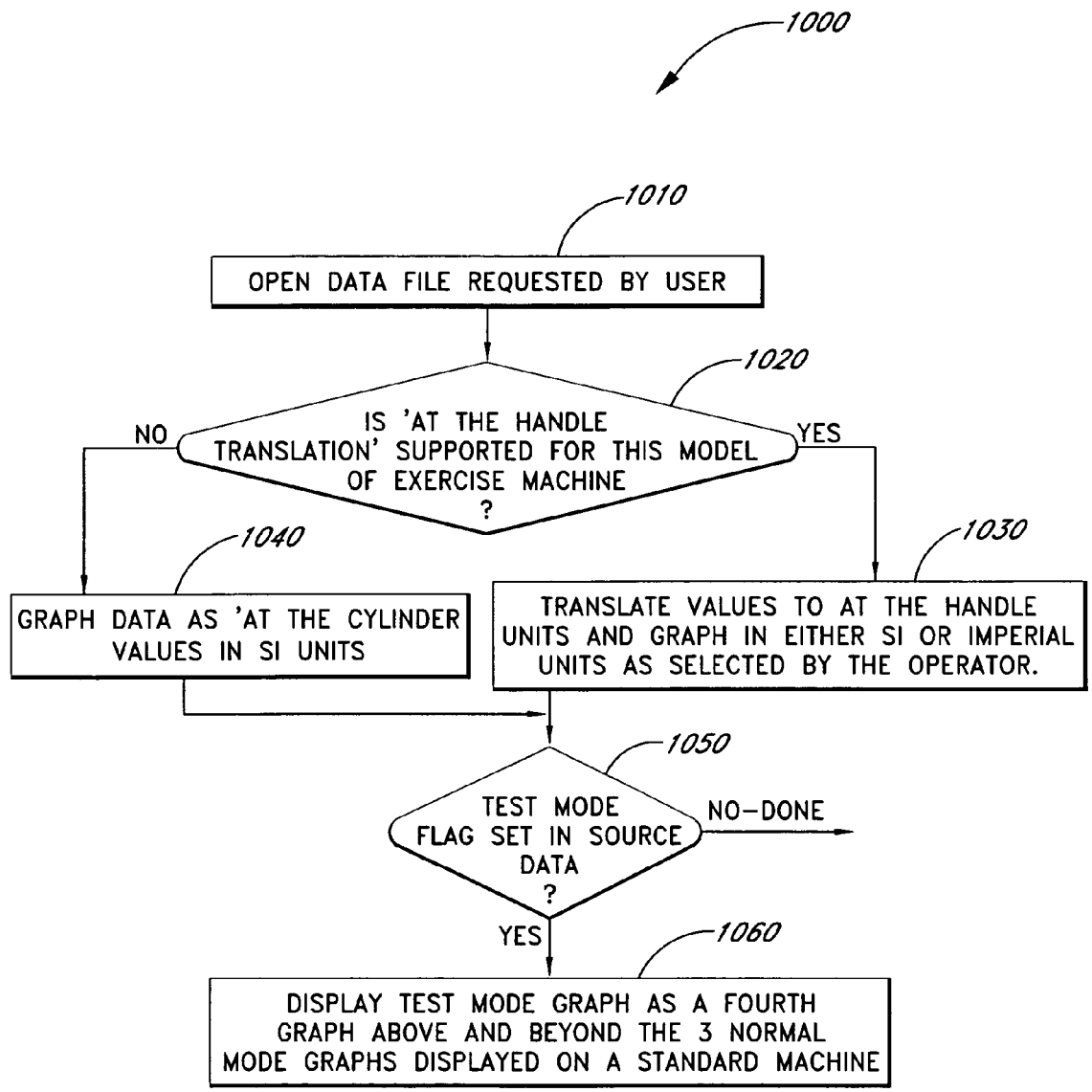
FIG. 10 illustrates a flow chart of a data graphing routine.

FIG. 10 illustrates a data graphing routine 1000 that is selectively performed by the external computer system 250 in response to a request to view the data collected by the apparatus 10 and transferred to the computer system 250. In a procedure 1010, the data graphing routine 1000 opens a data file requested by a user. For example, the data file may advantageously be identified by a selected combination of date, time, machine number and data key identification.

After opening the requested data file, the data graphing routine 1000 advances to a decision block 1020 wherein the external computer system 250 analyzes the exercise machine information included as part of the data file to determine whether support is provided for translating the collected data to "at the handle data." In particular, in the illustrated embodiment, the position transducers 230L, 230R measure the movement of the pistons within the respective pneumatic cylinders 82L, 82R. Similarly, the pressure transducers 220L, 220R measure the pressure within the respective pneumatic cylinders. Thus, the data collected by the data collecting routine 700 of FIG. 7 represents the velocity and the force at the pneumatic cylinders. Since the pistons of the pneumatic cylinders are coupled to the handgrips 60L, 60R (i.e., the handles) via the linkages provided by the connecting rods 80L, 80R, and the levers 40L, 40R, the velocities and forces at the pneumatic cylinders are different from the velocities and forces at the handles. The velocities and forces at the handles are computed by applying known trigonometric relationships to translate the forces and movements at the cylinders at respective upper ends of the levers 40L, 40R to the forces and movements at the handles at the lower ends of the levers. Since the angles of the connecting rods 80L, 80R with respect to the upper ends of the levers change as the connecting rods are pushed further into the respective cylinders, the translations must be computed for each position.

If the information required to translate the piston position and force data to handle position and force data is available for the particular exercise machine that collected the data being graphed, the graphing routine 1000 advances from the decision block 1020 to a procedure 1030 wherein the computer system 250 translates the collected "at the cylinder" to "at the handle" data. The translated data are then graphed in either metric (SI) units or imperial units as selected by the operator.

If the information required to translate the piston position and force data to handle position and force data is not available for the particular exercise machine that collected the data being graphed, the graphing routine 1000 advances from the decision block 1020 to a procedure 1040 wherein the computer system 250 graphs the data as "at the cylinder" values in metric (SI) units.

The data graphed by the computer system 250 in the procedure 1030 or in the procedure 1040 comprises the conventional data that is collected by the data collecting routine 700 for each exercise stroke. In particular, the graphs show the position, the calculated velocity and the calculated power as functions of time for each exercise stroke.

After completing either the procedure 1030 or the procedure 1040, the graphing routine 1000 advances to a decision block 1050 wherein the computer system 250 analyzes the data received from the exercise machine to determine whether the test mode flag was set in the collected data, as discussed above in connection with the procedure 820 in FIG. 8. If the test mode flag is not set, the graphing procedure is done for the currently accessed data file.

If the test mode flag is set in the collected data, the graphing procedure 1000 advances from the decision block 1050 to a procedure 1060 wherein the computer system 250 generates and displays power evaluation graphs produced in accordance with the power evaluation routine 800 of FIG. 8. In particular, rather than simply graphing the position, velocity and power as a function of time, the procedure 1060 graphs the peak velocity and the peak power for each handgrip as a function of force as illustrated in FIG. 11.

Figure 11:
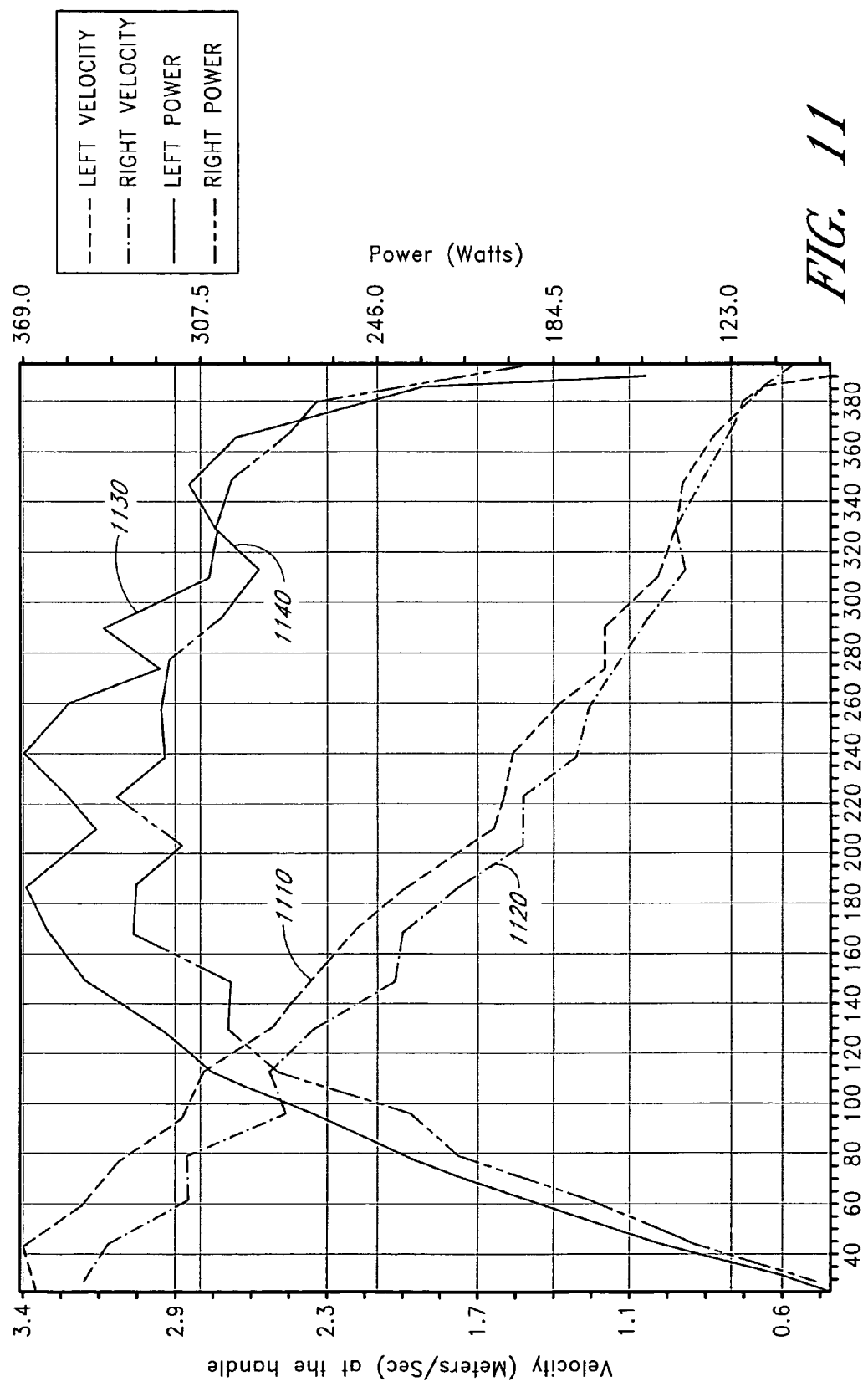
FIG. 11 illustrates graphs of the left handgrip velocity, the right handgrip velocity, the power of the left arm and the power of the right arm versus applied resistance.

In FIG. 11, the scale along the horizontal axis represents the resistance applied to each handle during a particular exercise stroke, the scale along the left vertical axis represents the peak velocity achieved during a particular exercise stroke, and the scale along the right vertical axis represents the peak power achieved during each exercise stroke. In FIG. 11, the force is presented as newtons, the velocity is presented as meters per second, and the power is presented as watts. It should be readily understood that the force, velocity and power in FIG. 11 can also be advantageously presented in imperial units of pounds, inches per second and watts, respectively. In FIG. 11, separate plots of velocity and power are provided for each arm, and the force in the horizontal axis is the force per arm rather than the total force.

A first graph 1110 is a plot of maximum velocity versus force for the left arm. A second graph 1120 is a plot of maximum velocity versus force for the right arm. A third graph 1130 is a plot of maximum power versus force for the left arm. A fourth graph 1140 is a plot of maximum power versus force for the right arm. Although the graphs in FIG. 11 are shown as continuous graphs, it should be understood that the graphs represent plots of discrete data points. The data points are interconnected with straight lines to enable the data to be more easily visualized. The graphs in FIG. 11 are based on data measured in increments of 10 pounds (approximately 44 newtons) in the total force applied to both arms. Thus, the data represent increments of 5 pounds (approximately 22 newtons) in the force applied to each arm.

In general, the velocity graphs 1110, 1120 show that the maximum velocities occur at very low forces, and that the maximum velocities generally decrease steadily as the resistance level increases.

In general, the power graphs 1130, 1140 start at relatively low values at the lower resistance levels. Since the amount of force is very low, the power is low. As the resistance level increases, the power increases generally steadily until the power reaches a maximum magnitude. As the resistance level continues to increase, the velocity continues to decrease and the power also decreases.

From the graphs in FIG. 11, it can be seen that the power reaches a maximum magnitude for different forces and velocities for the user's left arm and the user's right arm for the illustrated measurement sequence. For example, the graphs 1110 and 1120 indicate that at each resistance level, the left arm generally has a greater velocity than the velocity of the right arm. Thus, the left arm generally has more power at most resistance levels, as indicated by the graphs 1130 and 1140. Of course, the graphs of FIG. 11 will vary in accordance with the velocities and powers generated by the two arms of different users.

Assuming that the information in the graphs of FIG. 11 remains consistent over multiple measurements (e.g., that the particular user consistently moves the handgrips at the highest velocities for each increment of resistance level), an athletic trainer or a therapist may use the information in the graphs as a basis for determining that the particular user should focus on training at heavier weights (e.g., at resistances above approximately 240 newtons per arm in order to increase the power of both arms at higher resistances.

Subsequent measurements of power after recommended exercises can determine whether the results of the exercises exhibit a trend in the correct direction (e.g., increasing power in the ranges that were initially weaker).

The graphs of FIG. 11 also provide additional information. As discussed above, certain athletic activities, such as competitive weight lifting, require maximum power at high levels of force while maintaining a moderate velocity at those levels. On the other hand, other athletic activities, such as for example, throwing baseballs, require maximum power at much higher velocities without requiring high levels of force. In between, activities, such as putting the shot, require maximum power at higher levels of force than throwing baseballs while maintaining a relatively high velocity. The apparatus and method described herein can be advantageously used to gather data to develop graphs of the power of successful athletes and persons in other professions requiring physical ability to determine the resistance levels where such athletes and other persons produce the most power. This information can be advantageously used to evaluate aspiring athletes and other persons to determine how they compare to the anticipated power requirements for their activities. Armed with the information thus obtained, the person can develop a training program to properly condition the muscles to obtain the desired results.

Other population profiles can also be developed for other groups of persons (e.g., persons in particular age ranges or persons having other demographic characteristics). The power of a subject being evaluated can be compared with the norms of other persons in his or her population group to provide a relative measure of the power of the subject.

It should be understood that the foregoing description of a chest press apparatus is only one example of a measurement apparatus that can implement the system and method in accordance with aspects of the present invention. For example, one skilled in the art will appreciate that the foregoing features can be advantageously incorporated into a leg conditioning apparatus to enable the power of the legs to be measured to determine the velocity and resistance level where a subject develops the maximum power. After determining the velocity and resistance level for maximum power, a suitable conditioning program can be developed to increase the velocity and the strength to achieve a desired result.

Although described above with respect to athletic ability, it should be understood that the apparatus and method in accordance with aspects of the embodiments of the present invention can be advantageously used in other environments. For example, one problem encountered by a significant portion of an aging population is loss of strength and mobility. Failure to develop and maintain an adequate physical condition while younger becomes a far greater problem as the muscles deteriorate and weaken. It has been shown that strengthening exercises are beneficial to the overall health of an aging individual. However, as discussed above, measurement of strength alone is not sufficient in most cases to properly determine a person's physical ability. The above-described apparatus and method can be advantageously used to determine the resistance level and velocity where a person has the greatest power. A conditioning program can then be developed to improve the person's overall power rather than simply increasing strength or increasing speed. More particularly, by starting where the person has the most power, the conditioning program can start at a force and velocity where the person is most likely to be able to complete an exercise routine such that the person will also develop the confidence required to continue with the conditioning program. Other low-inertia exercise apparatuses that can be automatically controlled to selectively increment the resistance between each successive exercise stroke can also be advantageously used. For example, apparatuses using electromagnetic resistance devices, apparatuses using hydraulic resistance devices, or the like, may be used.

The invention may be embodied in other specific forms without departing from its spirit or essential characteristics. The described embodiments are to be considered in all respects only as illustrative and not restrictive. The scope of the invention is therefore indicated by the appended claims rather than by the foregoing description. All changes which come within the meaning and range of equivalency of the claims are to be embraced within that scope.

What is claimed is:

1. A method of evaluating the power of a muscle group of a person, comprising:
   initializing a resistance element to a first resistance level;
   moving an engagement assembly coupled to the resistance element at a highest achievable velocity through an exercise stroke;
   measuring a representative velocity at which the engagement assembly is moved through the exercise stroke and collecting data responsive to the representative velocity;
   increasing the resistance level of the resistance element;
   repeating the acts of moving, measuring and increasing until sufficient data are collected;
   calculating power for each exercise stroke based on the resistance level for each exercise stroke and the representative velocity for each exercise stroke;
   generating an output that represents at least the measured velocity and calculated power for a plurality of exercise strokes;
   determining a maximum power for the muscle group; and
   determining a velocity and a resistance level where the maximum power is produced.

2. A method of evaluating the power of a muscle group of a person, comprising:
   initializing a resistance element to a first resistance level;
   moving an engagement assembly coupled to the resistance element at a highest achievable velocity through an exercise stroke;
   measuring a representative velocity at which the engagement assembly is moved through the exercise stroke and collecting data responsive to the representative velocity;
   increasing the resistance level of the resistance element;
   repeating the acts of moving, measuring and increasing until sufficient data are collected;
   calculating power for each exercise stroke based on the resistance level for each exercise stroke and the representative velocity for each exercise stroke;
   generating an output that represents at least the measured velocity and calculated power for a plurality of exercise strokes; and
   determining a maximum power for the muscle group,
   wherein the engagement assembly is configured as a chest press, and wherein a first handgrip is provided for a left hand of a subject and a second handgrip is provided for a right hand of a subject, each handgrip being coupled to a respective resistance element, the act of measuring being performed independently for each handgrip to provide an independent power measurement for each arm of the subject.

3. A method of evaluating the power of a muscle group of a person, comprising:
   initializing a resistance element to a first resistance level;
   moving an engagement assembly coupled to the resistance element at a highest achievable velocity through an exercise stroke;
   measuring a representative velocity at which the engagement assembly is moved through the exercise stroke and collecting data responsive to the representative velocity;
   increasing the resistance level of the resistance element;
   repeating the acts of moving, measuring and increasing until sufficient data are collected, wherein sufficient data are collected when the resistance level is sufficient to preclude moving the engagement assembly through a complete exercise stroke;
   calculating power for each exercise stroke based on the resistance level for each exercise stroke and the representative velocity for each exercise stroke;
   generating an output that represents at least the measured velocity and calculated power for a plurality of exercise strokes; and
   determining a maximum power for the muscle group.

4. A method of evaluating the power of a muscle group of a person, comprising:
   initializing a resistance element to a first resistance level;
   moving an engagement assembly coupled to the resistance element at a highest achievable velocity through an exercise stroke;
   measuring a representative velocity at which the engagement assembly is moved through the exercise stroke and collecting data responsive to the representative velocity;
   increasing the resistance level of the resistance element;
   repeating the acts of moving, measuring and increasing until sufficient data are collected;
   calculating power for each exercise stroke based on the resistance level for each exercise stroke and the representative velocity for each exercise stroke;
   generating an output that represents at least the measured velocity and calculated power for a plurality of exercise strokes; and
   determining a maximum power for the muscle group,
   wherein the step of repeating the acts of moving, measuring and increasing comprises increasing the resistance level to a maximum resistance, and wherein the step of calculating power involves calculating a power at the maximum resistance.

5. A method of evaluating the power of a muscle group of a person, comprising:
   initializing a resistance element to a first resistance level;
   moving an engagement assembly coupled to the resistance element at a highest achievable velocity through an exercise stroke;
   measuring a representative velocity at which the engagement assembly is moved through the exercise stroke and collecting data responsive to the representative velocity;
   increasing the resistance level of the resistance element;
   repeating the acts of moving, measuring and increasing until sufficient data are collected;
   calculating power for each exercise stroke based on the resistance level for each exercise stroke and the representative velocity for each exercise stroke;
   generating an output that represents at least the measured velocity and calculated power for a plurality of exercise strokes;
   determining a maximum power for the muscle group; and
   determining a maximum velocity at which the engagement assembly is moved during a plurality of exercise strokes.

6. A method of evaluating the power of a muscle group of a person, comprising:
   initializing a resistance element to a first resistance level;
   moving an engagement assembly coupled to the resistance element at a highest achievable velocity through an exercise stroke, wherein the resistance element provides a generally consistent resistance against movement of the engagement assembly throughout the exercise stroke;
   measuring a representative velocity at which the engagement assembly is moved through the exercise stroke and collecting data responsive to the representative velocity;
   increasing the resistance level of the resistance element;
   repeating the acts of moving, measuring and increasing until sufficient data are collected;

calculating power for each exercise stroke based on the resistance level for each exercise stroke and the representative velocity for each exercise stroke;

generating an output that represents at least the measured velocity and calculated power for a plurality of exercise strokes; and determining a maximum power for the muscle group.

7. A method of evaluating the power of a muscle group of a person, comprising:

initializing a resistance element to a first resistance level;

moving an engagement assembly coupled to the resistance element at a highest achievable velocity through an exercise stroke, wherein the resistance element is a pneumatic cylinder in which the engagement assembly causes a piston within the pneumatic cylinder to move against air pressure in the pneumatic cylinder;

measuring a representative velocity at which the engagement assembly is moved through the exercise stroke and collecting data responsive to the representative velocity;

increasing the resistance level of the resistance element;

repeating the acts of moving, measuring and increasing until sufficient data are collected;

calculating power for each exercise stroke based on the resistance level for each exercise stroke and the representative velocity for each exercise stroke;

generating an output that represents at least the measured velocity and calculated power for a plurality of exercise strokes; and determining a maximum power for the muscle group.

8. The method as defined in claim 7, wherein the time between the act of measuring selectively increases as the resistance level increases to enable the muscle group to rest between successive acts of moving the engagement assembly.

9. The method as defined in claim 7, wherein the velocity is determined by periodically measuring a position of the piston, and the velocity is calculated based on the distance moved during a known time interval.

10. The method as defined in claim 7, wherein sufficient data are collected when the resistance level is incremented to a predetermined level.

11. The method as defined in claim 7, wherein sufficient data are collected when a predetermined number of exercise strokes are completed.

* * * * *

UNITED STATES PATENT AND TRADEMARK OFFICE
CERTIFICATE OF CORRECTION

| | | |
|---|---|---|
| PATENT NO. | : 8,523,789 B2 | Page 1 of 1 |
| APPLICATION NO. | : 10/694198 | |
| DATED | : September 3, 2013 | |
| INVENTOR(S) | : Keiser | |

It is certified that error appears in the above-identified patent and that said Letters Patent is hereby corrected as shown below:

In the Specification

In column 1 at line 67, Change "Bames" to --Barnes--.

In column 13 at line 13, Change "SOL," to --50L,--.

Signed and Sealed this
Fifteenth Day of April, 2014

Michelle K. Lee
*Deputy Director of the United States Patent and Trademark Office*